(12) United States Patent
Potenziano et al.

(10) Patent No.: US 10,201,564 B2
(45) Date of Patent: *Feb. 12, 2019

(54) METHODS OF USING INHALED NITRIC OXIDE GAS FOR TREATMENT OF ACUTE RESPIRATORY DISTRESS SYNDROME IN CHILDREN

(71) Applicant: Mallinckrodt Hospital Products IP Limited, Mulhuddart, Dublin (IE)

(72) Inventors: Jim Potenziano, Binghamton, NY (US); Ronald Bronicki, Houston, TX (US); James Baldassarre, Doylestown, PA (US)

(73) Assignee: Mallinckrodt Hospital Products IP Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 15/170,130

(22) Filed: Jun. 1, 2016

(65) Prior Publication Data

US 2016/0271169 A1    Sep. 22, 2016

Related U.S. Application Data

(63) Continuation of application No. 14/593,085, filed on Jan. 9, 2015, now Pat. No. 9,381,212.

(60) Provisional application No. 61/925,925, filed on Jan. 10, 2014.

(51) Int. Cl.
*A61K 33/00* (2006.01)
*A61K 9/00* (2006.01)

(52) U.S. Cl.
CPC .............. *A61K 33/00* (2013.01); *A61K 9/007* (2013.01)

(58) Field of Classification Search
None
See application file for complete search history.

(56) References Cited

U.S. PATENT DOCUMENTS

| | | | |
|---|---|---|---|
| 5,558,083 | A | 9/1996 | Bathe et al. |
| 5,570,683 | A | 11/1996 | Zapol |
| 5,732,693 | A | 3/1998 | Bathe et al. |
| 5,752,504 | A | 5/1998 | Bathe |
| 5,904,938 | A | 5/1999 | Zapol et al. |
| 6,103,275 | A | 8/2000 | Seitz et al. |
| 6,125,846 | A | 10/2000 | Bathe et al. |
| 7,523,752 | B2 | 4/2009 | Montgomery et al. |
| 8,282,966 | B2 | 10/2012 | Baldassarre et al. |
| 8,291,904 | B2 | 10/2012 | Bathe et al. |
| 8,293,284 | B2 | 10/2012 | Baldassarre et al. |
| 8,431,163 | B2 | 4/2013 | Baldassarre et al. |
| 8,573,209 | B2 | 11/2013 | Bathe et al. |
| 8,573,210 | B2 | 11/2013 | Bathe et al. |
| 8,776,794 | B2 | 7/2014 | Bathe et al. |
| 8,776,795 | B2 | 7/2014 | Bathe et al. |
| 8,795,741 | B2 | 8/2014 | Baldassarre |

(Continued)

OTHER PUBLICATIONS

Hall et al. (Acute Hypoxemic Respiratory Failure) Nov. 2013.*

(Continued)

*Primary Examiner* — Robert A Wax
*Assistant Examiner* — Melissa S Mercier

(57) ABSTRACT

The present invention provides a treatment of acute respiratory distress syndrome (ARDS) in children using dosing of nitric oxide at low concentrations, such as less than 10 ppm.

24 Claims, 6 Drawing Sheets

(comparative)

(56) References Cited

U.S. PATENT DOCUMENTS 8,846,112 B2 9/2014 Baldassarre
9,381,212 B2* 7/2016 Potenziano ............ A61K 33/00

OTHER PUBLICATIONS

Ream et al. (Low-Dose inhaled nitric oxide improves the oxygenation and ventilation of infants and children with acute, hypoxemic respiratory failures, Crit Care Med 1999, vol. 27, No. 5.*
ARDS Information Sheet, National Institute of Heath, www.nhlbi.nih.gov/book/export/html/4887, accessed from the Internet Jun. 17, 2015, 9 pages.
PCT International Search Report and Written Opinion in PCT/US2015/010839, dated Apr. 17, 2015, 11 pages.
PCT International Preliminary Report on Patentability in PCT/US2015/010839 dated Jul. 12, 2016, 7 pages.
Abman, Steven H., et al., "Acute effects of inhaled nitric oxide in childrenw ith severe hypoxemic respiratory failure", The Journal of Pediatrics, Jun. 1994, 881-888.
Adhikari, Neill K.J., et al., "Effect of nitric oxide on oxygenation and mortaltity in acute lung injury: systematic review and meta-analysis", BMJ, Mar. 23, 2007, 8 pages.
Day, Ronald W., et al., "A Randomized, Controlled Study of the 1-hour and 24-hour Effects of Inhaled Nitric Oxide Therapy in Children With Acute Hypoxemic Respiratory Failure", Clinical Investigations in Critical Care vol. 112 No. 5, Nov. 1997, 1324-1331.
Dobyns, Emily L., et al., "Multicenter randomized controlled trial of the effects of inaled nitric oxide therapy on gas exchange in children with acute hypoxemic respiratory failure", The Journal of Pediatrics vol. 134 Iss. 4, Apr. 1999, 406-412.
Fioretto, "Inhaled Nitric Oxide in Pediatrics", Journal de Pediatria vol. 79 Supl. 2, 2003, S177-S186.
Frostell, Claes, et al., "Inhaled Nitric Oxide: A Selective Pulmonary Vasodilator Reversing Hypoxic Pulmonary Vasoconstriction", Circulation vol. 83 No. 6, Jun. 1991, 2038-2047.
Ream, Robert S., et al., "Low-dose inhaled nitric oxide improves the oxygenation and ventilation of infances and children with acute, hypoxemic respiratory failure", Crit. Care Med. vol. 27 No. 5, 1999, 989-996.
Tang, et al., "Randomised trial of three doses of inhaled nitric ocide in acute respiratory disease syndrome", Arch. Dis. Child vol. 79, 1998, 415-418.
Thomas, Neal J., et al., "Acute Lung Injury in Children—Kids Really Aren't Just "Little Adults"", Pediatric Critical Care Medicine vol. 14 No. 4, May 2013, 429-432.
INOvent Delivery System: Operation and Maintenance Manual (CGA Variant), 2000, 180 pages.
INOmax DS (Delivery System): Operation Manual (800 ppm INOmax (nitric oxide) for Inhalation), 2010, 112 pages.
INOmax DSIR Operation Manual (800 ppm INOmax (nitric oxide) for inhalation), 2012, 136 pages.
Using the INOpulse DS Subject Guide, 2012, 50 pages.
INOmax Label, (Nitric Oxide) for Inhalation, 2009, 9 pages.
INOmax Label, Nitric Oxide Gas, INO Therapeutics, 2013, 2 pages.
Amin, Z. and Amanda, A.P., Comparison of New ARDS Criteria (Berlin) with Old Criteria (AECC) and its Application in Country with Limited Facilities, Journal of General and Emergency Medicine, 2016, 3 pages.
Fioretto, J.R. and De Carvalho, W.B., Temporal evolution of acute respiratory distress syndrome definitions, J Pediatr (Rio J), 2013, vol. 89, No. 6, pp. 523-530.
Hu, X. et al, Incidence, management and mortality of acute hypoxemic respiratory failure and acute respiratory distress syndrome from a prospective study of Chinese paediatric intensive care network, Acta Pædiatrica/, 2010, vol. 99, pp. 715-721.
Zhu, Y. et al, Mortality and morbidity of acute hypoxemic respiratory failure and acute respiratory distress syndrome in infants and young children, Chinese Medical Journal 2012, vol. 125, No. 13, pp. 2265-2271.

* cited by examiner

FIG. 1 (comparative)

| Study Population | Placebo (n=29) | iNO (n=26) |
|---|---|---|
| Age (yrs) (mean) | 5.8 (5.1) | 3.8 (4.1) |
| Sex | | |
| Female | 18 | 12 |
| Male | 11 | 14 |
| **Primary Diagnosis *[1]** | | |
| Pneumonia/Cx+ | 11 (38) | 10 (38) |
| Pneumonia/Cx- | 9 (31) | 7 (27) |
| Sepsis | 4 (14) | 3 (12) |
| Trauma | 2 (7) | 0 (0) |
| Other Dx | 5 (14) | 8 (31) |
| Race | | |
| American Indian | 1 | 0 |
| Asian | 3 | 1 |
| Black | 8 | 7 |
| Hispanic | 4 | 8 |
| White | 13 | 9 |
| Other | 0 | 1 |

*[1] Patients may have more than 1 diagnosis

FIG. 2

| Ventilation Settings and Gas Exchange at Enrollment | Placebo | iNO |
|---|---|---|
| Time to enrollment* | 1.9 (2.0) | 2.1 (1.4) |
| OI* | 25.6 (14.9) | 22.0 (8.4) |
| CMV | 20 | 19 |
| PEEP | 10.9 (2.8) | 10.6 (2.9) |
| MAP | 20.6 (5.6) | 17.8 (3.7) |
| FiO$_2$ | 71.0 (22.8) | 83.5 (20.3) |
| P plat | 32.0 (3.3) | 28.7 (1.5) |
| HFOV | 9 | 7 |
| MAP | 27.7 (4.5) | 26.3 (2.6) |
| FiO$_2$ | 92.6 (10.6) | 53.6 (22.4) |

*Values expressed as mean +/- SD*
*OI, oxygenation index; CMV, Conventional mechanical ventilation; PEEP, Positive end expiratory pressure (cm H$_2$O); MAP, mean airway pressure (cm H$_2$O); FiO$_2$, partial pressure of inspired oxygen (%). P plat, Plateau pressure (cm H$_2$O); HFOV, high frequency oscillatory ventilation; time to enrollment: duration of MV prior to randomization (days);*
*\* denotes p > 0.05*

FIG. 3

Results

| | Placebo (n=29) | iNO (n=24) | 95% CI | P-value | RR |
|---|---|---|---|---|---|
| Days alive and ventilator free at 28 days* Mean days +/- SD | 9.11 +/- 9.47 | 14.7 +/- 8.11 | -9.99, -0.002 | 0.05 | - |
| Survival n (%) | 21 (72.4%) | 22 (91.7%) | 0.98-1.63 | 0.07 | 1.27 |
| Rate of ECMO free survival n (%) | 15 of 29 (51.7) | 22 of 24 (91.7) | 1.22-2.57 | < 0.01 | 1.77 |

*For subjects who died, days alive without mechanical ventilation were assigned a value of zero. Time on mechanical ventilation was calculated using the time of first intubation and last extubation.

FIG. 6

METHODS OF USING INHALED NITRIC OXIDE GAS FOR TREATMENT OF ACUTE RESPIRATORY DISTRESS SYNDROME IN CHILDREN

CROSS-REFERENCE TO RELATED APPLICATIONS

This application is a continuation under 35 U.S.C. § 120 of U.S. patent application Ser. No. 14/593,085, filed Jan. 9, 2015, which claims the benefit under 35 U.S.C. § 119(e) to U.S. Provisional Application No. 61/925,925, filed Jan. 10, 2014, the entire contents of which are incorporated herein by reference in their entirety.

FIELD

The present invention relates to methods of using inhaled nitric oxide gas to treat and/or prevent acute respiratory distress syndrome in children.

BACKGROUND

Acute respiratory distress syndrome (ARDS), previously known as adult respiratory distress syndrome, is a life-threatening lung condition that prevents enough oxygen from getting to the lungs and into the blood. ARDS may result from an injury to or an infection in the lungs of a patient.

Inhaled nitric oxide (iNO) transiently improves oxygenation in adults with ARDS, but does not significantly decrease mortality. The impact of iNO on outcomes in children with ARDS has not been previously evaluated in a randomized, non-crossover trial.

SUMMARY

One or more embodiments of the present invention are directed to a method for treating a child with ARDS or preventing ARDS in a child at risk of developing ARDS via administration of a low dose of inhaled nitric oxide (iNO). In one or more embodiments, the dose of iNO is less than about 10 ppm, such as in the range from about 0.1 ppm to about 8 ppm or in the range from dose in the range from about 2 ppm to about 6 ppm. In some embodiments, the NO dose is less than about 8 ppm. In one or more embodiments, the NO dose is about 5 ppm.

The iNO may be administered for a relatively short-term treatment, such as for a treatment period of up to 28 days. In exemplary embodiments, the NO is administered for a treatment period in the range from 2 days to 2 months.

The iNO may be administered during patient inspiration, expiration, or portions thereof. In one or more embodiments, the iNO is administered during only a portion of inspiration, such as only administering iNO during the first half of inspiration.

According to one or more embodiments, the child may be less than 16 years old. Exemplary ages for the child include those in the range from 44 weeks post-conceptional age to 16 years of age.

In one or more embodiments, the child is not subjected to extracorporeal membrane oxygenation during NO administration.

In one or more embodiments, NO increases the number of days that the child is alive and ventilator-free at 28 days after the start of NO administration.

Also provided is a method of increasing extracorporeal membrane oxygenation-free (ECMO-free) survival in children with ARDS or at risk of developing ARDS, the method comprising administering a gas comprising NO to a child in need thereof at a dose of less than 10 ppm NO. In one or more embodiments, the NO dose may be the in range from about 0.1 ppm to about 8 ppm, such as about 5 ppm.

Also provided is a method of increasing the number of ventilator-free days in children with ARDS or at risk of developing ARDS, the method comprising administering a gas comprising nitric oxide (NO) to a child in need thereof at a dose of less than 10 ppm NO. In one or more embodiments, the NO dose may be the in range from about 0.1 ppm to about 8 ppm, such as about 5 ppm.

BRIEF DESCRIPTION OF THE DRAWINGS

FIG. 2 shows a summary of the patient population in a study investigating the administration of 5 ppm iNO versus placebo for children with AHRF according to one or more exemplary embodiments of the invention.

FIG. 3 shows the ventilation settings and gas exchange at enrollment for the AHRF in children study.

FIG. 6 shows a summary of the results for the AHRF in children study.

DETAILED DESCRIPTION

Figure 1:
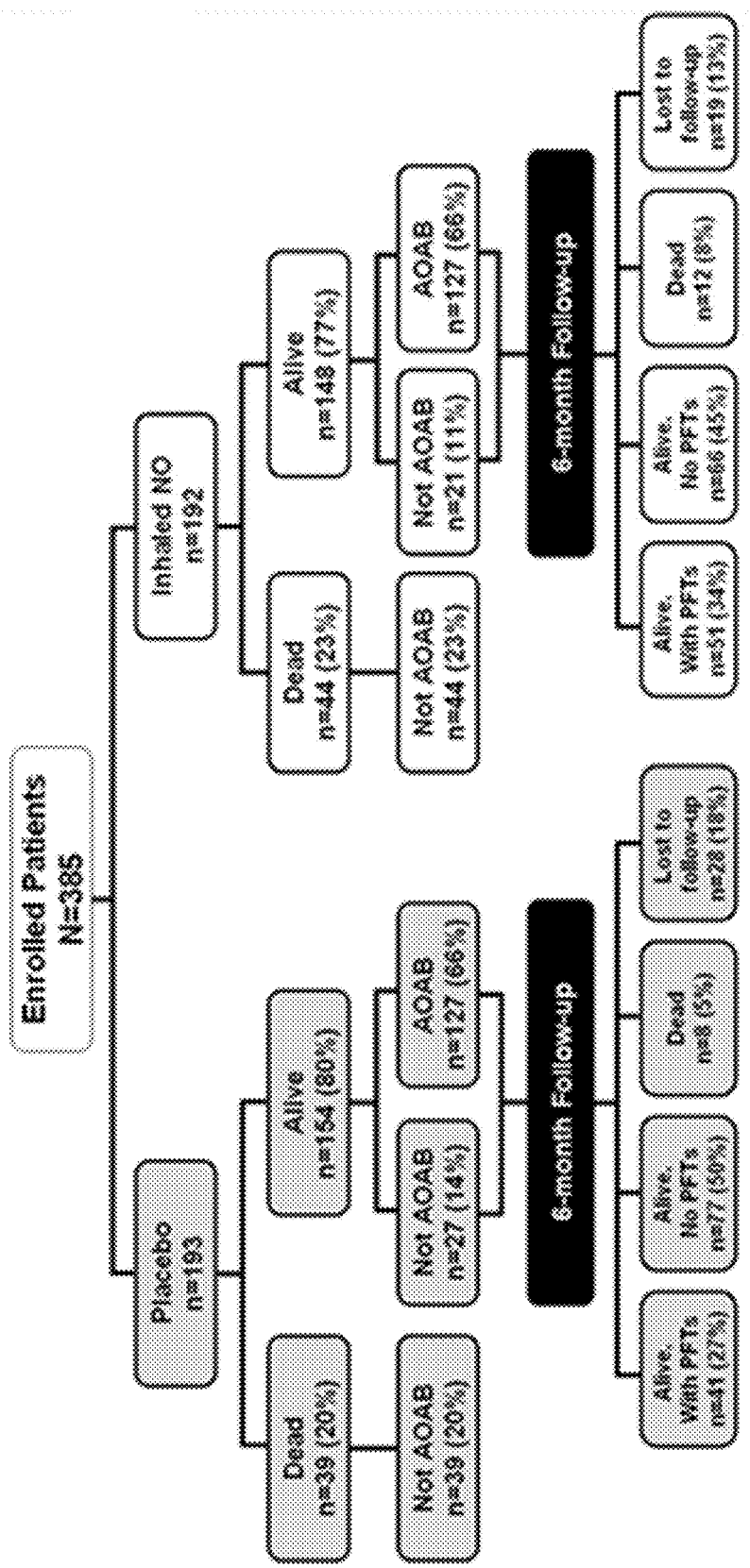
FIG. 1 shows the final disposition of all subjects in a study investigating the administration of 5 ppm iNO versus placebo for adults with ARDS.

The present invention is directed to the unexpected finding that short term treatment of ARDS in children using inhaled nitric oxide (iNO) gas resulted in an increased number of days that a child is ventilator-free at 28 days after the start of iNO therapy. It was also unexpectedly found that the rate of extracorporeal membrane oxygenation oxygenation-free (ECMO-free) survival is significantly higher in children treated with iNO therapy than children administered a placebo. As previous studies investigating the use of iNO for treating ARDS in adults did not meet their primary endpoints of reduced mortality or increase in days alive and off assisted breathing, it was surprising that a clinical study investigating iNO therapy for children with ARDS approached statistical significance for the number of days patient remains alive and extubated to day 28 after initiating study therapy.

Accordingly, one or more embodiments of the present invention provide for the treatment and/or prevention of pediatric ARDS using iNO.

Definitions

As used herein the following terms shall have the definitions set forth below.

As used herein, the term "therapeutic composition" refers to a drug delivered to a patient. The use of the term "therapeutic composition" is in concurrence with the Food and Drug Administration's (FDA) definition of a drug: articles intended for use in the diagnosis, cure, mitigation, treatment, or prevention of disease. Such drugs may include gases comprising nitric oxide, such as nitric oxide in a diluent or carrier gas such as nitrogen or helium. The NO-containing gas may be provided by any known method, such as from a gas cylinder or chemically generating the NO at or near the place of administration. The NO-containing gas may be at a higher concentration in the cylinder or other gas source and be diluted to a delivery concentration prior to use. The drug may be provided by a drug delivery device.

The device designation as defined herein is in concurrence with the Food and Drug Administration's (FDA) definition of a device: A device is defined as an instrument, apparatus, implement, machine, contrivance, implant, in vitro reagent, or other similar or related article, including a component part, or accessory which is:

recognized in the official National Formulary, or the United States Pharmacopoeia, or any supplement to them, intended for use in the diagnosis of disease or other conditions, or in the cure, mitigation, treatment, or prevention of disease, in man or other animals, or intended to affect the structure or any function of the body of man or other animals, and which does not achieve any of its primary intended purposes through chemical action within or on the body of man or other animals and which is not dependent upon being metabolized for the achievement of any of its primary intended purposes.

As described herein, the device may be a nitric oxide delivery device that administers a gas comprising nitric oxide. Suitable nitric oxide delivery devices include the INOvent®, INOmax® DS and INOmax DSIR® delivery devices, available from Ikaria Inc. in Hampton, N.J.

As used herein, the term "treating" refers to the treatment of a disease or condition of interest in a patient (e.g., a mammal) having the disease or condition of interest, and includes, for example one or more of the following:

(i) preventing the disease or condition from occurring in a mammal, in particular, when such mammal is predisposed to the condition but has not yet been diagnosed as having it;

(ii) inhibiting the disease or condition (i.e., arresting its development);

(iii) reducing the extent of disease or condition (i.e., causing regression of the disease or condition); or (iv) ameliorating the symptoms resulting from the disease or condition (i.e., relieving pain without addressing the underlying disease or condition).

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, "short term treatment" refers to treatment periods up to about 1, 2, 3, 4, 5, 6, 7, 8, 9, 10, 15, 20 or 25 days or one month, two months or three months. The treatments described herein may have a certain minimum and/or maximum treatment periods. Minimum treatment periods may include about 1, 2, 3, 4, 5, 7, 8, 9, 10, 11, 12, 15, 18 or 24 hours or about 1, 2, 3, 4, 5, 6, 7, 8, 9, 10, 11, 12, 13, 14, 15, 20, 25, 28 or 30 days. Maximum treatment periods may include about 12, 18 or 24 hours or about 1, 2, 3, 4, 5, 6, 7, 8, 9, 10, 11, 12, 13, 14, 15, 20, 25, 28 or 30 days or about 2, 4, 6, 8, 10 or 12 weeks or about 1, 2, 3, 4, 5 or 6 months.

As used herein, "chronic treatment" refers to treatment periods of greater than three months.

As used herein, the term "patient" refers to a human to whom treatment according to the methods of the present invention is provided.

As used herein, the term "subject" is used interchangeably with "patient".

As used herein, the term "child" refers to a human that is under 18 years of age. In one or more embodiments, the child to be treated may be between the ages of 44 weeks post-conceptional age to 16 years of age. "Post-conceptional age" refers to the age of an infant relative to the date of conception plus the chronological age. In various embodiments, the lower age range for the child may be 36, 37, 38, 39, 40, 41, 42, 43, 44, 45, 46, 47, 48, 49 or 50 weeks post-conceptional age or 1, 2, 3, 4, 5, 6, 7 or 8 weeks chronological age or 1, 2, 3, 4, 5, 6, 7, 8, 9, 10, 11, 12, 15, 18, 21 or 24 months chronological age. The term "chronological age" refers to the age relative to the date of birth. In various embodiments, the upper age range for the child may be 18, 17, 16, 15, 14, 13, 12, 11, 10, 9, 8, 7, 6, 5, 4, 3, 2 or 1 years of age.

As used herein, the term "administering" refers to any mode of transferring, delivering, introducing or transporting the therapeutic composition, device or other agent to a subject. Administration of the therapeutic composition, device or other agent may be conducted concurrently or sequentially in time. Additionally, administration of the therapeutic composition, device and other agent(s) may be via the same or different route(s).

As used herein, the term "effective amount" refers to that amount of which, when administered to a patient (e.g., a mammal) for a period of time is sufficient to cause an intended effect or physiological outcome. The amount of therapeutic composition which constitutes an "effective amount" will vary depending on the condition and its severity, the manner of administration, and the patient (e.g., the age of the mammal to be treated), but can be determined routinely by one of ordinary skill in the art having regard to his own knowledge and to this disclosure.

For example, in one embodiment, the term "effective amount" refers to the amount that can achieve a measurable result. In one embodiment, an "effective amount" is, for example, an amount that when administered to a human subject in need of medical treatment in a controlled Phase 2 or Phase 3 clinical trial produces a statistically significant benefit on a predefined clinical endpoint.

As used herein, the term "indications" includes, but is not limited to, pulmonary disease, acute lung injury (ALI), acute respiratory distress syndrome (ARDS) and acute hypoxemic respiratory failure (AHRF). ARDS is related to the medical condition AHRF, and ARDS often has a perfusion-related component such as pulmonary hypertension (PH).

ARDS and ALI may be determined by any acceptable criteria by one of ordinary skill in the art. On such set of criteria include (1) acute bilateral infiltrates on chest radiographic appearance, (2) the ratio of the partial pressure of oxygen in arterial blood to the fraction of inspired oxygen ($PaO_2/FiO_2$ or PF ratio) of less than 200 for ARDS and less than 300 for acute lung injury (ALI), and (3) noncardiogenic pulmonary edema based on an assessment of the left atrial filling pressure by means of a wedged pulmonary artery catheterization or clinical assessment. Typically in children, chest radiographs or echocardiograms are substituted for pulmonary artery catheterization to assess left atrial filling pressures, especially given the relatively low incidence of cardiogenic pulmonary edema in children. The accepted medical criteria used to determine any of the diseases or disorders described herein may adjust due to developments in the medical community or advances in technology The methods and compositions of the present invention may be used to treat or prevent a variety of diseases and disorders, including any disease or disorder that has been treated using any of a gaseous form of nitric oxide, a liquid nitric oxide composition or any medically applicable useful form of nitric oxide, including any described in U.S. Pat. No. 6,103,275.

As used herein, the term "tissue" refers to any mammalian body tissue, desirably a human body tissue, including damaged tissue. A body tissue, according to the teachings to the present invention, may be, but is not limited to, muscle tissue, particularly cardiac tissue and, more particularly, myocardial tissue, such as left ventricular wall myocardial tissue.

As used herein, the term "damaged tissue" refers to any damaged mammalian body tissue, including, for example, damaged pulmonary tissue, and particularly, damaged lung tissue.

Gases and Detection of Gases

Methods for safe and effective administration of NO by inhalation are well known in the art. See, e.g., Zapol, U.S. Pat. No. 5,570,683; Zapol et al., U.S. Pat. No. 5,904,938; Bathe et al., U.S. Pat. No. 5,558,083; Frostell et al., 1991, Circulation 83:2038-2047. NO for inhalation is available commercially (INOmax®, Ikaria, Inc., Hampton, N.J.). Each of these references is incorporated by reference in its entirety. In the present invention, NO inhalation preferably is in accordance with established medical practice.

iNO is commercially available as INOmax® for the treatment of hypoxic respiratory failure in term and near-term neonates. See, e.g., INOmax®, package insert (www.inomax.com), which is incorporated by reference in its entirety.

Inhaled nitric oxide may be formulated for use by dilution in nitrogen and/or other inert gases and may be administered in admixture with oxygen, air, and/or any other appropriate gas or combination of multiple gases at a desired ratio.

In one or more embodiments, the NO is administered at a dose less than 10 ppm. Exemplary dose ranges include minimum doses of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9 or 9.5 ppm and maximum doses of about 1, 1.5, 2, 2.5, 3, 3.5, 4, 4.5, 5, 5.5, 6, 6.5, 7, 7.5, 8, 8.5, 9, 10, 11, 12, 13, 14, 15, 20, 25, 30, 35, 40, 45 or 50 ppm.

The nitric oxide may be administered during the patient's entire inspiration, or may be administered for only a portion of the patient's inspiration. In one or more embodiments, the NO is not administered in the last about 10%, 15%, 20%, 25%, 30%, 35%, 40%, 45%, 50%, 55%, 60%, 65%, 70%, 75%, 80%, 85% or 90% of inspiration (i.e. the NO is administered only at the beginning of the patient's inspiration). NO administration can start and end at any point during inspiration and expiration.

In one or more embodiments, the nitric oxide therapy is begun early on in the treatment of ARDS and/or prevention of ARDS. It is believed that administering nitric oxide as described herein may have a greater benefit if the nitric oxide is administered before ARDS develops or early in the development of ARDS.

In some embodiments, iNO administration may be used as an alternative to extracorporeal membrane oxygenation (ECMO) therapy for children with ARDS. A patient's respiratory and/or pulmonary parameters may be checked frequently to determine if ECMO therapy is necessary. For example, the patient's parameters may be checked multiple times per days (such as 2, 3, 4, etc. times per day) or may be checked daily or every few days (such as every 2, 3, 4, etc. days). iNO may also be administered in addition to ECMO therapy.

EXAMPLES

Comparative Example 1—Adults ARDS Study

Introduction

Inhaled nitric oxide (iNO) is a vasodilator indicated for treatment of term and near-term neonates with hypoxic respiratory failure associated with clinical or echocardiographic evidence of pulmonary hypertension. In these patients, iNO has been shown to improve oxygenation and reduce the need for extracorporeal membrane oxygenation therapy. NO binds to and activates cytosolic guanylate cyclase, thereby increasing intracellular levels of cyclic guanosine 3',5'-monophosphate (cGMP). This, in turn, relaxes vascular smooth muscle, leading to vasodilatation. Inhaled NO selectively dilates the pulmonary vasculature, with minimal systemic vasculature effect as a result of efficient hemoglobin scavenging. In acute lung injury (ALI) and acute respiratory distress syndrome (ARDS), increases in partial pressure of arterial oxygen ($PaO_2$) are believed to occur secondary to pulmonary vessel dilation in better-ventilated lung regions. As a result, pulmonary blood flow is redistributed away from lung regions with low ventilation/perfusion ratios toward regions with normal ratios.

Many pharmacologic treatments have been investigated in ARDS patients, including alprostadil, acetylcysteine, corticosteroids, surfactant, dazoxiben, and acyclovir. A meta-analysis of trials completed through 2004 indicated no statistically significant mortality benefit with any of the above-mentioned treatments.

Study

A large-scale, randomized, blinded, placebo-controlled study was carried out in the Intensive Care Units (ICUs) of 46 US hospitals to evaluate the efficacy of low-dose (5 ppm) iNO in 385 patients with moderately severe Acute Lung Injury (ALI). The primary endpoint of this study was number of days alive and off assisted breathing. Results of an intent-to-treat analysis revealed that inhaled NO (iNO) had no significant benefit versus control (nitrogen gas) as it related to mortality, days alive and off assisted breathing, or days alive and meeting oxygenation criteria for extubation. However, iNO treatment did result in a significant increase ($p<0.05$) in partial pressure of arterial oxygen ($PaO_2$) during the initial 24 hours of treatment that resolved by 48 hours.

Safety Results

Safety results for the initial 28-day study period have been reported and are summarized briefly here. A total of 630 adverse events (AEs) were reported for patients treated with iNO versus 666 events for those who received placebo. Respiratory system AEs occurred in 51% versus 61% of patients receiving iNO and placebo, respectively, primarily due to higher frequencies of pneumonia, pneumothorax, and apnea in the placebo group. Frequency of other AEs was similar in both groups.

Patients

Patients had acute lung injury (ALI), defined by a modification of American-European Consensus Conference criteria ($PaO_2$/inspired oxygen concentration [$FiO_2$] ratio of ≤250 mm Hg), due to causes other than severe sepsis. Patients with evidence of non-pulmonary system failure at the time of randomization and sepsis-induced ARDS were excluded. Patients were also excluded if they had sustained hypotension requiring vasopressor support, hemodynamic profiles supporting severe sepsis, severe head injury, severe burns, or evidence of other significant organ system dysfunction at baseline.

Treatment

Patients were randomly assigned to receive either inhaled placebo gas (nitrogen) or 5 ppm of iNO (INO Therapeutics Inc., Port Allen, La.). All patients, healthcare professionals, and investigators were blinded to the assigned treatment. Inhaled NO was administered via INOvent® delivery system (Datex-Ohmeda, Madison, Wis.) that blended treatment gas (nitrogen or NO at 100-ppm balance nitrogen) 1:20 with ventilator gases to achieve a target ppm value in the inspiratory limb of the ventilator.

All patients using the iNO delivery system received mechanical ventilatory support. Treatment continued with active or placebo gas until one of the following criteria were met: [1] end of trial (28 days); [2] death; or [3] adequate oxygenation (arterial oxygen saturation by pulse oximetry [$SpO2$]≥92% or $PaO2$ of ≥63 mm Hg) without treatment gas at ventilator settings of FiO2≤0.4 and positive end-expiratory pressure (PEEP) of ≤5 cm H2O. Decreases in treatment gas continued in 20% decrements (titrated down by 1 ppm for inhaled NO) every 30 minutes until either the treatment gas concentration reached 0% or oxygenation criteria were not satisfied. If oxygenation criteria were not met, treatment gas concentration was titrated up until they were again achieved. Increments of upward titration were determined by the clinician, based on degree of arterial desaturation.

Respiratory Parameters Measured During Hospitalization

Baseline oxygenation measures included $PaO_2$, arterial partial pressure of $CO_2$ ($PaCO_2$), $SpO_2$, $FiO_2$, PEEP, $PaO_2/FiO_2$ ratio, ventricular rate, tidal volume, and mean airway pressure. Respiratory parameters ($FiO_2$, PEEP, and $PaO_2/FiO_2$ ratio) were recorded on case report forms every 12 hours during mechanical ventilation.

Statistical Methods

Between-group differences in baseline clinical and demographic characteristics were assessed with the Fisher's exact test and the chi-square test for categorical variables and with the Wilcoxon rank sum test for continuous variables. Baseline oxygenation and respiratory/oxygenation parameters in the two groups were compared using Wilcoxon rank sum tests. The areas under the curve (AUCs) of FiO2, PEEP, and PaO2/FiO2 ratio were calculated using the trapezoidal rule. The null hypothesis that the respective AUCs were normally distributed was rejected employing the Shapiro-Wilk test. A Wilcoxon rank sum test was utilized to assess the differences in each median AUC between treatment groups. A p value <0.05 was considered significant.

Results

Demographics and Baseline Characteristics

Final disposition of all subjects in the original study and 6-month follow-up is shown in FIG. 1. Baseline patient characteristics are summarized in Table 1. Patients in the two treatment groups were well matched for all demographic variables. The only significant between-group difference was for weight (76.35±19.16 kg [mean±SD] versus 85.67±24.10 kg for iNO and placebo, respectively; p=0.0489). There were no significant differences between groups with respect to ARDS etiology. There were no differences between groups with respect to severity of illness, frequency of co-morbid chronic respiratory conditions (i.e., asthma, chronic obstructive pulmonary disease, or other obstructive or restrictive lung disease), or use of inhaled corticosteroids. More subjects had a history of tobacco use in the iNO group (26 versus 17, p=0.41).

Baseline Oxygenation Parameters

Baseline oxygenation parameters, including $PaO_2$, $PaCO_2$, $SpO_2$, $FiO_2$, PEEP, and $PaO_2/FiO_2$ ratio, are summarized in Table 2. The patients included in this analysis were severely ill with mean baseline $PaO_2/FiO_2$ ratios of 140.5±43.4 (iNO) and 136.1±40.4 (placebo). Except for a clinically insignificant difference in $SpO_2$, there were no significant between-group differences with respect to baseline oxygenation parameters.

Baseline Respiratory Parameters

Baseline respiratory parameters, including ventilator rate, tidal volume, and mean airway pressure are summarized in Table 3. There were no significant differences between groups for any of these measures.

Respiratory Parameters During Mechanical Ventilation

There were no significant differences between groups for aggregate per-patient changes from baseline parameters in supplemental oxygen, PEEP, or PaO2/FiO2 ratio. However, when calculating the duration of exposure over the length of mechanical ventilation for total FiO2 (6.3+4.5 days versus 7.6+4.7 days for iNO and placebo groups, respectively; p=0.151), total PEEP (96.3+75.9 versus 113.4+81.1 mm Hg, p=0.261) and total PaO2/FiO2 ratio (2637+1729 versus 2950+1774, p=0.358), the iNO group had less cumulative exposure to all three variables (Table 4).

Summary

Clinical trials evaluating numerous interventions have repeatedly failed to demonstrate significant benefit in decreasing mortality in ARDS patients. This clinical trial, as well as a meta-analysis of 12 randomized controlled trials in ALI or ARDS patients indicated no significant benefit of iNO in decreasing mortality.

Inhaled NO did not improve short-term mortality in patients with ARDS

Tables

Table 1 is a summary of baseline demographic and clinical characteristics of the study group.

Table 2 is a summary of baseline oxygenation parameters of the study group (placebo versus treated).

Table 3 is a summary of baseline respiratory parameters of the study group (placebo versus treated).

Table 4 is a summary of the duration of exposure parameters during gas administration.

TABLE 1

Baseline Demographic and Clinical Characteristics

| Parameter | | Placebo | Inhaled NO | P Value |
|---|---|---|---|---|
| Age, y | N | 41 | 51 | |
| | Mean ± SD | 47.8 ± 16.7 | 45.3 ± 15.3 | 0.494 |
| | Range | 18.4-84.0 | 16.8-77.9 | |
| Sex, n (%) | Male | 19 (46%) | 25 (49%) | 0.836 |
| | Female | 22 (54%) | 26 (51%) | |
| Race, n (%) | Caucasian | 35 (85%) | 42 (82%) | 0.847 |
| | Black | 4 (10%) | 5 (10%) | |
| | Other | 2 (5%) | 4 (8%) | |
| Height, cm | N | 39 | 51 | |
| | Mean ± SD | 168.7 ± 11.4 | 169.4 ± 9.2 | 0.912 |
| Weight, kg | N | 41 | 51 | |
| | Mean ± SD | 85.7 ± 24.1 | 76.4 ± 19.2 | 0.049 |
| Causes of ARDS,* n (%) | | | | |
| Pneumonia | | 20 (49%) | 15 (29%) | 0.084 |
| Toxic gas inhalation | | 0 (0%) | 0 (0%) | 1.000 |
| Acute pancreatitis | | 1 (2%) | 3 (6%) | 0.626 |

TABLE 1-continued

Baseline Demographic and Clinical Characteristics

| Parameter | Placebo | Inhaled NO | P Value |
|---|---|---|---|
| Massive blood transfusion | 5 (12%) | 10 (20%) | 0.404 |
| Fat emboli | 1 (2%) | 2 (4%) | 1.000 |
| Aspiration pneumonitis | 9 (22%) | 9 (18%) | 0.610 |
| Pulmonary contusion | 6 (15%) | 12 (24%) | 0.307 |
| Postpartum ARDS | 2 (5%) | 0 (0%) | 0.196 |
| Multiple trauma | 14 (34%) | 15 (29%) | 0.657 |
| Elective or emergency surgical procedures | 9 (22%) | 20 (39%) | 0.114 |
| Preexisting lung disease | 41 (100%) | 49 (96%) | 0.501 |
| Preexisting steroid use | 3 (7%) | 6 (11.8%) | 0.334 |
| Asthma | 4 (10%) | 5 (10%) | 1.000 |
| COPD | 6 (15%) | 6 (12%) | 0.761 |
| Tobacco use | 17 (41%) | 26 (51%) | 0.405 |
| Other lung disease[†] | 10 (5%) | 8 (4%) | 0.810 |

ARDS = acute respiratory distress syndrome;
COPD = chronic obstructive pulmonary disorder;
NO = nitric oxide.
*Patients may have more than one cause of ARDS.
[†]Patients may have more than one preexisting disease including: cancer, bronchitis, amiodarone toxicity, and status/post lung resection.

TABLE 2

Baseline Oxygenation Parameters

| Parameter | Statistics | Placebo | Inhaled NO | P Value |
|---|---|---|---|---|
| $PaO_2$, mm Hg | N | 41 | 50 | |
| | Mean ± SD | 84.8 ± 21.4 | 90.6 ± 19.1 | |
| | Median | 81 | 86 | 0.068 |
| $PaCO_2$, mm Hg | N | 41 | 50 | |
| | Mean ± SD | 39.9 ± 7.7 | 40.8 ± 8.4 | |
| | Median | 41 | 39 | 0.728 |
| $SpO_2$, % | N | 41 | 50 | |
| | Mean ± SD | 95.1 ± 2.6 | 96.5 ± 2.6 | |
| | Median | 96 | 97 | 0.012 |
| $FiO_2$ | N | 41 | 50 | |
| | Mean ± SD | 0.65 ± 0.13 | 0.68 ± 0.16 | |
| | Median | 1 | 1 | 0.517 |
| PEEP, cm $H_2O$ | N | 41 | 51 | |
| | Mean ± SD | 9.5 ± 1.7 | 9.8 ± 2.5 | |
| | Median | 10 | 10 | 0.748 |
| $PaO_2/FiO_2$ ratio | N | 41 | 50 | |
| | Mean ± SD | 136.1 ± 40.4 | 140.5 ± 43.4 | |
| | Median | 132 | 130 | 0.774 |

$FiO_2$ = inspired oxygen concentration;
$PaCO_2$ = arterial pressure of $CO_2$;
$PaO_2$ = partial pressure of arterial oxygen;
PEEP = positive-end expiratory pressure;
$SpO_2$ = pulse oximetric oxygen saturation.

TABLE 3

Baseline Respiratory Parameters.*

| Parameter | Statistics | Placebo | Inhaled NO | P Value |
|---|---|---|---|---|
| Ventilator rate, breaths/min | N | 41 | 50 | 0.069 |
| | | 14.6 ± 4.4 | 13.1 ± 4.2 | |
| Tidal volume, mL/kg | N | 39 | 49 | 0.548 |
| | | 9.1 ± 1.7 | 10.3 ± 2.5 | |
| Mean airway pressure, cm $H_2O$ | N | 37 | 46 | 0.488 |
| | | 18.3 ± 7.1 | 16.9 ± 5.2 | |

*Values are mean ± SD unless otherwise indicated.
NO = nitric oxide.

TABLE 4

Duration of Exposure Parameters During Study Gas Administration.*

| Parameter | Placebo (N = 41) | Inhaled NO (N = 51) | P Value |
|---|---|---|---|
| Inhaled NO, ppm/d | 0 | 114 ± 102 | NA |
| $FiO_2$ | 7.6 ± 4.7 | 6.34 ± 4.5 | 0.151 |
| PEEP, mm Hg | 113 ± 81 | 96.33 ± 75.9 | 0.261 |
| $PaO_2/FiO_2$ ratio | 195 ± 46 | 262 ± 407 | 0.358 |

*Values are mean ± SD unless otherwise indicated.
$FiO_2$ = inspired oxygen concentration;
NO = nitric oxide;
$PaO_2$ = partial pressure of arterial oxygen;
PEEP = positive-end expiratory pressure.

Example 1—Pediatric AHRF Study

Synopsis

Methodology

This was a prospective, multicenter, randomized, double-blind, placebo-controlled, parallel-group study of the safety and efficacy of inhaled nitric oxide in pediatric subjects with acute hypoxemic respiratory failure (AHRF). The subjects were randomized to receive either 5 ppm inhaled nitric oxide or placebo.

Number of Subjects (Planned and Analyzed)

350 total subjects (175 per treatment arm) were planned. Because of low enrollment (and not for safety reasons) the trial was ended when 55 subjects were enrolled. A summary of the study population is provided in FIG. 2 and the ventilation settings and gas exchange at enrollment are shown in FIG. 3.

Diagnosis and Main Criteria for Inclusion

Pediatric subjects admitted to the Pediatric Intensive Care Unit (PICU) with AHRF requiring intubation.

Test Product, Dose and Mode of Administration

Nitric Oxide for inhalation at 5 ppm was administered continuously into the inspiratory limb of the ventilator circuit in mechanically ventilated subjects using a blinded version of the INOvent® delivery system.

Duration of Treatment

Subjects received 100% treatment gas (nitric oxide 5 ppm or placebo [nitrogen gas]) until Day 28 or extubation, whichever occurred first.

Reference Therapy, Dose and Mode of Administration

Placebo consisting of 100% Grade 5 nitrogen gas was administered continuously into the inspiratory limb of the ventilator circuit in mechanically ventilated subjects using a blinded version of the INOvent® delivery system at a rate equivalent to a 5 ppm dose of nitric oxide.

Summary—Conclusions
Efficacy Results:

Efficacy data were collected and summarized in place of a full efficacy analysis. The mean duration of intubation, days in the PICU, and frequencies of high frequency oscillatory ventilation, extracorporeal membrane oxygenation, and pneumothorax were lower for the nitric oxide group than for the placebo group, whereas the duration of supplemental oxygen and the frequency of ventilator-associated pneumonia at discharge were higher for the nitric oxide group than for the placebo group.

Figure 4:
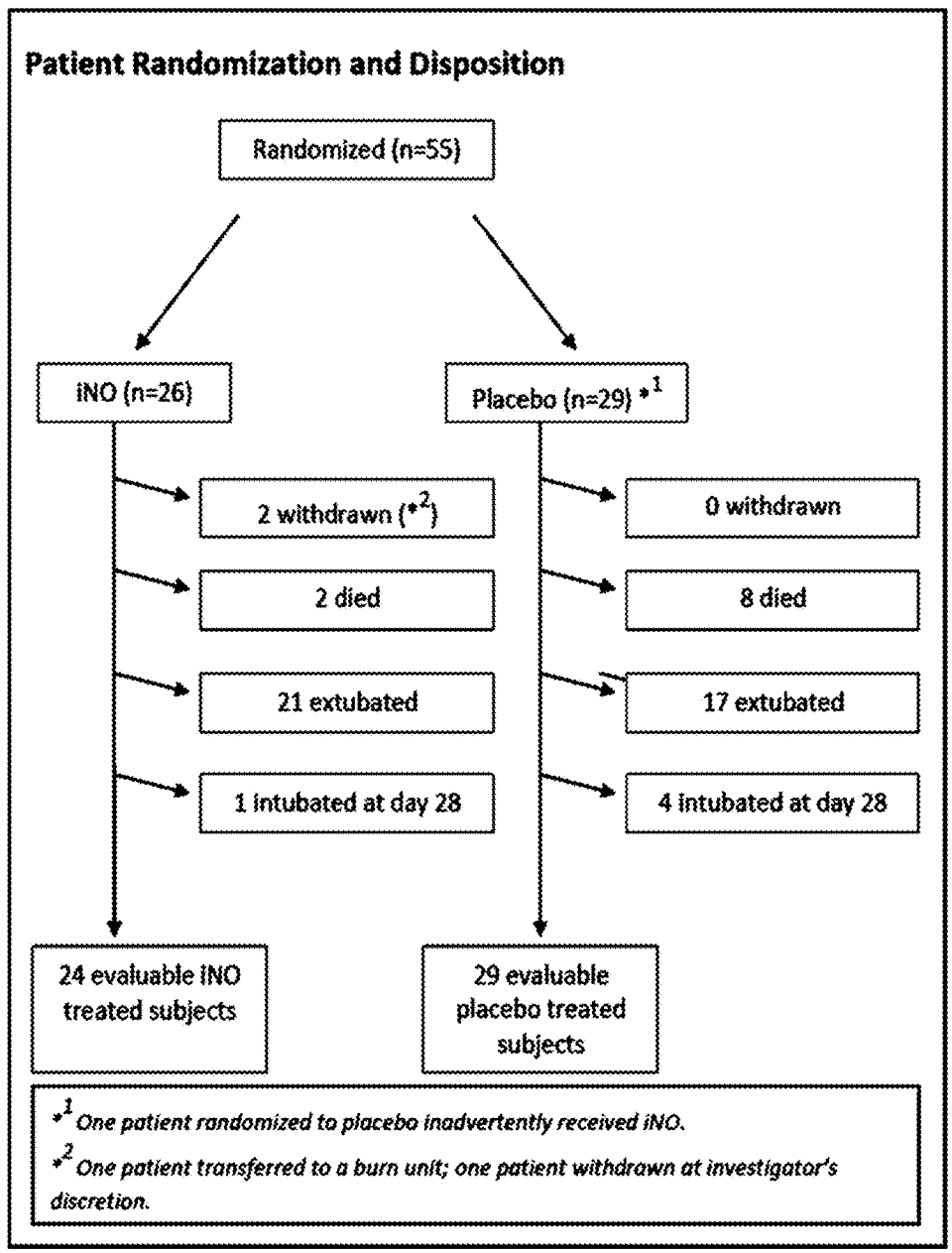
FIG. 4 shows a summary of the patient randomization and disposition for the AHRF in children study.
Figure 5:
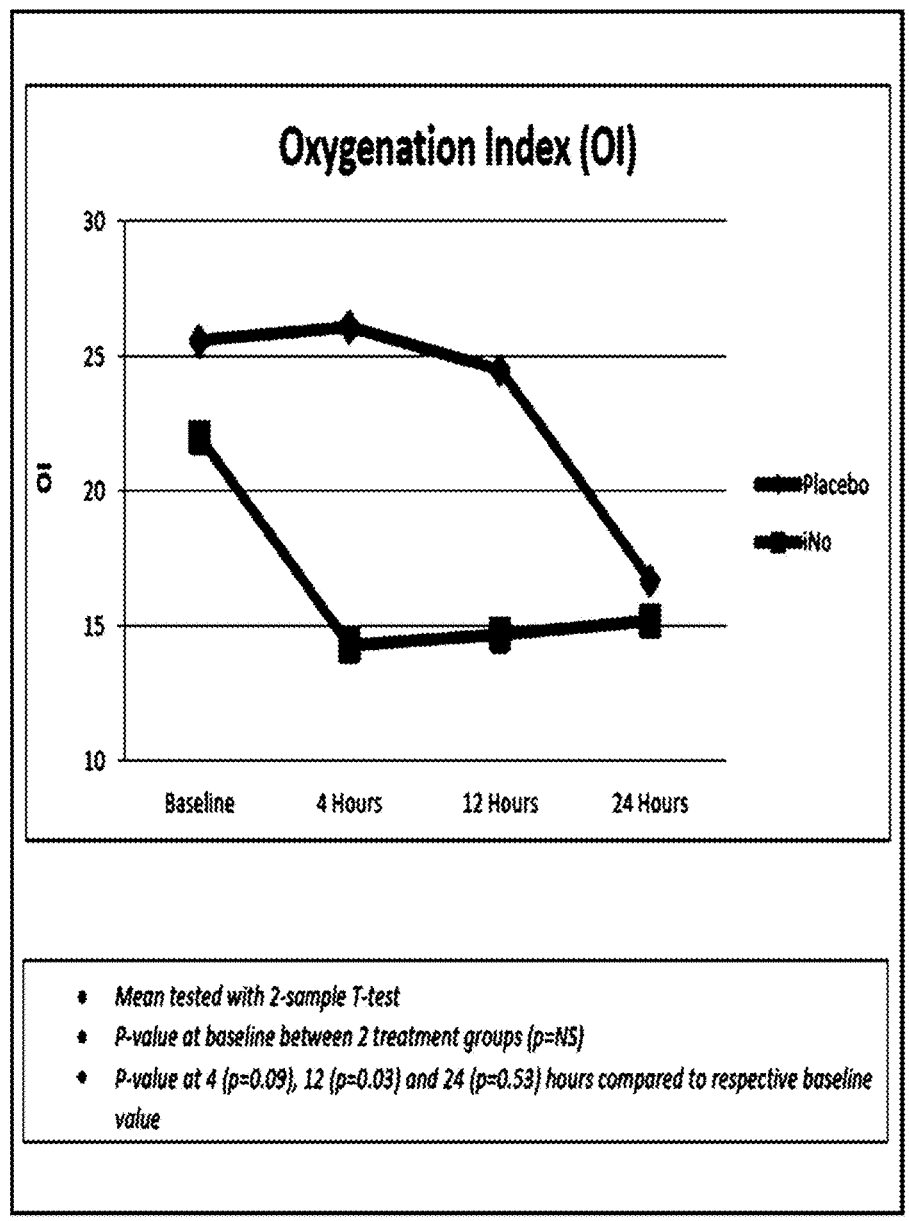
FIG. 5 shows the oxygenation index at baseline, 4 hours, 12 hours and 24 hours for the AHRF in children study.

29 patients received placebo and 26 iNO. A summary of the patient randomization and disposition is shown in FIG. 4. 2 patients randomized to iNO were withdrawn from the study due to premature termination of study gas. The mean baseline oxygenation index (OI) were 25.6+/−14.9 and 22.0+/18.4, placebo and iNO groups, respectively, p=NS. As shown in FIG. 5, there was a greater improvement in OI compared to baseline values in the iNO group at 4 hours (26.1+/−19.5 and 14.3+/−5.9, placebo and iNO groups, respectively, p=0.09) that became significant at 12 hours (24.5+/−22.0 v. 14.7+/−6.0, p=0.04). By 24 hours there was no significant difference in oxygenation between groups (16.7+/−9.9 and 15.2+/−10.8, placebo and iNO groups, respectively, p=0.53). Days alive and ventilator free at 28 days was greater in those randomized to iNO 9.1+/−9.5 versus 14.2+/18.1 days (p=0.05). Survival at 28 days was 22 of 24 in the iNO group and 21 of 29 in the placebo group (p=0.07) and the rate of ECMO free survival was significantly greater in those randomized to iNO 22 of 24 versus 15 of 29, p<0.01. These results are shown in FIG. 6.

Safety Results:

Subjects who received inhaled nitric oxide were no more likely to experience adverse events (AEs) than were those who received placebo, with 21 subjects in the placebo group (72.4%) reporting 93 AEs and 16 subjects in the nitric oxide group (61.5%) reporting 52 AEs. Four AEs, reported by 2 subjects in the placebo group, were suspected to have a relationship to treatment. The frequencies of treatment discontinuation due to AEs were 6.9% for the placebo group and 3.9% for the nitric oxide group. Compared with subjects treated with placebo, subjects treated with nitric oxide reported fewer serious AEs during the study (27.6% vs. 3.9%) and had a higher survival rate (72.4% vs. 88.5%). No death, serious AE, severe AE, or AE resulting in treatment discontinuation was suspected to be related to study treatment. The percent methemoglobin levels were within normal limits in both the placebo and the nitric oxide groups. These levels were well below levels that would have necessitated discontinuation of treatment.

Conclusion:

The safety profile of inhaled nitric oxide 5 ppm appears to compare favorably with that of placebo, with regard to methemoglobin levels, frequency of AEs and, particularly, mortality rates. No serious concerns about the use of inhaled nitric oxide were generated by the results of this study, and it appears that inhaled nitric oxide 5 ppm is safe and well tolerated by children with AHRF.

Unexpectedly, iNO shortened the duration of mechanical ventilation (MV) and improved the rate of survival, both of which approached statistical significance. The rate of ECMO free survival was significantly greater in those randomized to iNO. It is believed that this is the first randomized, non-crossover study to evaluate the impact of iNO on outcomes in pediatric ARDS. Previous studies incorporated a crossover design, precluding an analysis of outcomes.

Study Details

This was a prospective, multicenter, randomized, double-blind, placebo-controlled, Phase III study to assess the effects of nitric oxide for inhalation in the treatment of acute hypoxic respiratory failure (AHRF) in pediatric subjects. The study population consisted of male and female pediatric subjects, aged 44 weeks postconceptional age to 16 years age, who were admitted to the pediatric intensive care unit (PICU) and who required intubation because of AHRF. The inclusion/exclusion criteria are described in the Patients section below.

Standardized ventilatory management and weaning procedures were used. Ventilatory management was used based on an "open lung approach" using positive end-expiratory pressure (PEEP) to increase lung volume and limiting tidal volumes to reduce plateau pressures. Subjects received nitric oxide for inhalation at 5 ppm or placebo (100% Grade 5 nitrogen gas) into the inspiratory limb of the ventilator circuit using a blinded version of the INOvent® delivery system. The subjects were treated until Day 28 or extubation, whichever occurred first. Subjects were assessed daily using a spontaneous breathing trial, according to the institution's standard of care. Arterial blood gases (ABG), ventilator settings, methemoglobin, oxygenation index, systolic blood pressure, diastolic blood pressure, Pediatric Risk of Mortality (PRISM) III score, and subject positioning (prone or supine) were performed/recorded at specified times during the study. Selected centers also performed plasma cytokine assays, bronchoalveolar lavage fluid (BALF) assays, and a 6-month follow-up assessment.

Patients

Inclusion criteria for patients were as follows:
1. 44 weeks post-conceptional age to 16 years of age
2. Oxygenation Index (OI)≥12 cm $H_2O$/mmHg (as determined by two separate measurements taken 30 minutes to 4 hours apart)
3. Recent chest x-ray (within 24 hours) showing at least unilateral infiltrates
4. Mechanically ventilated (oral or nasopharyngeal)<7 days Exclusion criteria for patients were as follows:
1. Immunocompromised
2. Received a bone marrow transplant
3. Active oncological condition
4. Persistent right to left intracardiac shunt
5. Cardiovascular surgery within the last 14 days
6. Status asthmaticus
7. Decision by primary care physician not to provide full support (futility)
8. Received treatment with nitric oxide for inhalation or other investigational medications with 24 hours prior to study initiation.
9. Chronically ventilated
10. Pregnant Study Design and Schedule of Assessments:

The following assessments were made at baseline: arterial blood gases, ventilator settings, methemoglobin, prone position, PRISM III score, oxygenation index, systolic and diastolic blood pressure, bronchoalveolar lavage fluid assay and plasma cytokine.

The following assessments were made at 4 hours±1 hour after the start of therapy: arterial blood gases, ventilator settings and methemoglobin.

The following assessments were made at 12 hours±2 hours after the start of therapy: arterial blood gases and ventilator settings.

The following assessments were made at 24 hours±2 hours after the start of therapy: arterial blood gases, ventilator settings, methemoglobin, systolic and diastolic blood pressure and plasma cytokine.

The following assessments were made at 48 hours after the start of therapy: bronchoalveolar lavage fluid assay.

The following assessments were made at 72 hours after the start of therapy: plasma cytokine.

The following assessments were made on Day 5 after the start of therapy: bronchoalveolar lavage fluid assay.

The following assessments were made on Day 7 after the start of therapy: plasma cytokine.

Prone positioning was evaluated daily to determine whether prone ≥8 hours within a 24-hour period.

The following assessments were made at the end of treatment: plasma cytokine.

The following assessments were made during the follow-up visit: pulmonary function tests (subjects >6 years of age), vital signs (respiratory rate and spot oxygen saturation), and chest X-ray.

Extubation was considered when:
 i. Pressure support of <10 cm $H_2O$
 ii. $FiO_2$<0.60
 iii. PEEP<6 cm $H_2O$
 iv. Nitric oxide has been discontinued for 30 minutes Extubation occurred within 12 hours of meeting the above criteria. If a patient met the above criteria but was not extubated within 12 hours, the reason (i.e. airway protection, surgery, secretions clearance, etc.) was documented.

Disposition of Patients

Fifty-five subjects were enrolled and randomized to treatment. The intent-to-treat population consisted of 30 subjects randomized to treatment with placebo and 25 subjects randomized to treatment with nitric oxide 5 ppm. One subject, who was originally randomized to receive placebo, received nitric oxide in error. This subject was allowed to continue treatment with nitric oxide throughout the trial. Therefore, the safety population consisted of 29 subjects who received placebo and 26 subjects who received nitric oxide.

Of the 55 subjects enrolled, 21 (72.4%) in the placebo group and 21 (80.8%) in the nitric oxide group either completed 28 days of the study or were successfully extubated. Of the remaining subjects, 8 (27.6%) in the placebo group and 2 (7.7%) in the nitric oxide group died, and 3 subjects in the nitric oxide group discontinued treatment for reasons other than death. Subject outcome is summarized in Table 5.

TABLE 5

Subject Outcome by Actual Treatment Received

| Outcome | Placebo n = 29 | Nitric Oxide 5 ppm n = 26 |
|---|---|---|
| Successful extubation, n (%) | 17 (58.6%) | 20 (76.9%) |
| Day 28, n (%) | 4 (13.8%) | 1 (3.8%) |
| Total discontinued, n (%) | 8 (27.6%) | 5 (19.2%) |
| Best interest of subject, n (%) | 0 (0) | 1 (3.8%) |
| Tracheotomy, n (%) | 0 (0) | 1 (3.8%) |
| Transferred to burn hospital, n (%) | 0 (0) | 1 (3.8%) |
| Death, n (%) | 8 (27.6%) | 2 (7.7%) |

Efficacy Evaluation

Demographics and Other Baseline Characteristics

The baseline characteristics of the study population are summarized in Table 6.

TABLE 6

Subject Characteristics by Actual Treatment Received

| Variable | | Placebo n = 29 | Nitric Oxide 5 ppm n = 26 |
|---|---|---|---|
| Sex, n (%) | Female | 18 (62.1%) | 12 (46.2%) |
| | Male | 11 (37.9%) | 14 (53.8%) |
| Race, n (%) | American Indian | 1 (3.4%) | 0 (0) |
| | Asian | 3 (10.3%) | 1 (3.8%) |
| | Black | 8 (27.6%) | 7 (26.9%) |
| | Hispanic | 4 (13.8%) | 8 (30.8%) |
| | Other | 0 (0) | 1 (3.8%) |
| | White | 13 (44.8%) | 9 (34.6%) |
| Diagnosis, [a] n (%) | Other diagnosis | 4 (13.8%) | 8 (30.8%) |
| | Positive pneumonia culture | 11 (37.9%) | 10 (38.5%) |
| | Negative pneumonia culture | 9 (31.0%) | 7 (26.9%) |
| | Sepsis | 4 (13.8%) | 3 (11.5%) |
| | Trauma | 2 (6.9%) | 0 (0) |
| | Unknown | 1 (3.4%) | 0 (0) |
| Age (yrs) | N | 29 | 26 |
| | Mean (SD) | 5.8 (5.1) | 3.8 (4.1) |
| | Median | 4.2 | 2.5 |
| | Range | (0.1, 16.2) | (0.1, 13.5) |

[a] Subjects may have more than one diagnosis.

The medical history of the study population is summarized in Table 7.

TABLE 7

Medical History by Actual Treatment Received

| | Subjects with History n (%) | |
|---|---|---|
| Medical History | Placebo | Nitric Oxide 5 ppm |
| Non-operative cardiovascular disease | 2 (6.9%) | 0 (0) |
| Chromosomal anomaly | 5 (17.2%) | 4 (15.4%) |
| Cancer | 1 (3.4%) | 0 (0) |
| Previous PICU admission | 15 (34.5%) | 3 (11.5%) |
| Pre-PICU CPR | 1 (3.4%) | 3 (11.5%) |
| Post-operative | 1 (3.4%) | 1 (3.8%) |
| Diabetic ketoacidosis | 1 (3.4%) | 0 (0) |
| Admission from inpatient unit | 15 (51.7%) | 7 (26.9%) |
| N/A | 3 (10.3%) | 4 (15.4%) |

Abbreviations:
PICU = pediatric intensive care unit;
CPR = cardiopulmonary resuscitation;
N/A = not applicable The concomitant corticosteroid medications are summarized in Table 8.

TABLE 8

Frequencies of Concomitant Corticosteroid Medications by Actual Treatment Received

| Type | Coded Steroid Name | Placebo[a] | Nitric Oxide 5 ppm[a] |
|---|---|---|---|
| Extubated | Dexamethasone | 6 (20.7%) | 4 (15.4%) |
| | Methylprednisolone | 0 (0) | 1 (3.8%) |

TABLE 8-continued

Frequencies of Concomitant Corticosteroid Medications by Actual Treatment Received

| Type | Coded Steroid Name | Placebo[a] | Nitric Oxide 5 ppm[a] |
|---|---|---|---|
| | Methylprednisolone, sodium succinate | 1 (3.4%) | 0 (0) |
| | Prednisone | 1 (3.4%) | 0 (0) |
| Late Lung Disease | Dexamethasone | 2 (6.9%) | 0 (0) |
| | Fludrocortisone | 1 (3.4%) | 0 (0) |
| | Fluticasone propionate | 1 (3.4%) | 1 (3.8%) |
| | Hydrocortisone | 1 (3.4%) | 1 (3.8%) |
| | Methylprednisolone | 2 (6.9%) | 2 (7.7%) |
| | Methylprednisolone Sodium succinate | 4 (13.8%) | 3 (11.5%) |
| | Prednisolone | 1 (3.4%) | 0 (0) |
| | Prednisone | 1 (3.4%) | 4 (15.4%) |
| Neither | Hydrocortisone | 1 (3.4%) | 0 (0) |
| | Prednisone | 0 (0) | 1 (3.8%) |

[a]Subjects with multiple administrations of the same steroid are counted only once.

Efficacy Results and Tabulations of Individual Patient Data

Full efficacy analyses were not performed. However, efficacy data were collected and summarized. As shown in Table 9, the mean number of days of intubation, days in the PICU, and frequencies of high-frequency oscillatory ventilation (HFOV), extracorporeal membrane oxygenation (ECMO), and pneumothorax were lower for the nitric oxide group than for the placebo group, whereas the mean number of days of supplemental oxygen and the frequency of VAP at discharge were higher for the nitric oxide group than for the placebo group. The survival rate was 72.4% for the placebo group and 88.5% for the nitric oxide group.

TABLE 9

Efficacy Data by Actual Treatment Received

| Variable | Placebo | Nitric Oxide 5 ppm |
|---|---|---|
| Number of days originally intubated, in PICU, and on supplemental O₂ | | |
| Number of days originally intubated - Mean (SD) | 15.8 (11.2) | 13.6 (6.8) |
| Number of days in PICU - Mean (SD) | 25.6 (15.4) | 17.8 (8.3) |
| Number of days on supplemental O₂ - Mean (SD) | 18.8 (15.0) | 19.6 (13.4) |
| Discharge evaluation | | |
| N | 29 | 26 |
| Survival, n (%) | 21 (72.4%) | 23 (88.5%) |
| Died (cause of death related to pulmonary condition), n (%) | 1 (3.4%) | 0 (0) |
| Receiving supplemental O₂ on Day 28, n (%) | 8 (27.6%) | 11 (42.3%) |
| Intubated on Day 28, n (%) | 5 (17.2%) | 2 (7.7%) |
| HFOV at any time during treatment, n (%) | 18 (62.1%) | 11 (42.3%) |
| ECMO at any time during treatment, n (%) | 7 (24.1%) | 0 (0) |
| Clinical sepsis, n (%) | 4 (13.8%) | 4 (15.4%) |
| VAP, n (%) | 1 (3.4%) | 5 (19.2%) |
| Pneumothorax, n (%) | 10 (34.5%) | 3 (11.5%) |

Abbreviations:
PICU = pediatric intensive care unit;
HFOV = high-frequency oscillatory ventilation;
ECMO = extracorporeal membrane oxygenation;
VAP = ventilator-associated pneumonia.

Safety Evaluation

Extent of Exposure

The mean duration of treatment was 13 days for subjects in both treatment groups (Table 10). Note that one subject from the placebo group and one subject who received nitric oxide were excluded from this table because their study drug end date and time were unknown.

TABLE 10

Extent of Exposure by Actual Treatment Received

| Duration of treatment (days) | Placebo | Nitric Oxide 5 ppm |
|---|---|---|
| N | 28 | 25 |
| Mean (SD) | 13.2 (8.8) | 12.7 (7.0) |
| Median | 10.7 | 12.7 |
| Range | (0.4, 28.1) | (2.8, 29.0) |

TABLE 11

Durations by Actual Treatment Received

| | Placebo | Nitric Oxide 5 ppm |
|---|---|---|
| Duration of treatment (days) | | |
| N | 28 | 25 |
| Mean (SD) | 13.2 (8.8) | 12.7 (7.0) |
| Median | 10.7 | 12.7 |
| Range | (0.4, 28.1) | (2.8, 29.0) |
| Days originally intubated | | |
| N | 19 | 20 |
| Mean (SD) | 15.8 (11.2) | 13.6 (6.8) |
| Median | 11.9 | 13.7 |
| Range | (1.8, 48.8) | (3.2, 23.2) |
| Days in PICU | | |
| N | 17 | 22 |
| Mean (SD) | 25.6 (15.4) | 17.8 (8.3) |
| Median | 24.6 | 17.3 |
| Range | (10.3, 55.2) | (4.9, 37.3) |
| Days on supplemental O₂ | | |
| N | 11 | 10 |
| Mean (SD) | 18.8 (15.0) | 19.6 (13.4) |
| Median | 16.3 | 18.1 |
| Range | (1.8, 57.8) | (4.3, 50.7) |

Adverse Events

There were 93 AEs reported in 21 of the 29 subjects who received placebo (72.4%). A total of 52 AEs were reported in 16 of the 26 subjects who received nitric oxide (61.5%). Four of the AEs (reported in 2 subjects in the placebo group) were suspected to have a relationship to treatment.

There were 21 serious adverse events (SAEs) reported in 8 of the 29 subjects who received placebo (27.6%) and 2 SAEs reported in 1 of the 26 subjects who received nitric oxide (3.9%). There were 27 severe AEs reported in 10 subjects who received placebo (34.5%) and 4 severe AEs reported in 2 subjects who received nitric oxide (7.7%). Two AEs reported in 2 subjects who received placebo (6.9%) and 2 AEs reported in 1 subject who received nitric oxide (3.9%) resulted in discontinuation of study treatment. None of the serious or severe AEs was suspected to be related to study treatment. An overall summary of AEs is presented in Table 12.

TABLE 12

Overview of Adverse Events by Actual Treatment Received

| Category[a] | Placebo n = 29 | Nitric Oxide 5 ppm n = 26 |
|---|---|---|
| Subjects treated, n (%) | 29 (100%) | 26 (100%) |
| Subjects with one or more AEs, n (%) | 21 (72.4%) | 16 (61.5%) |
| Subjects with one or more SAEs, n (%) | 8 (27.6%) | 1 (3.9%) |
| Subjects withdrawn due to AEs, n (%) | 2 (6.9%) | 1 (3.9%) |
| Subjects with one or more severe AEs, n (%) | 10 (34.5%) | 2 (7.7%) |
| Subjects with one or more AEs suspected to be related to study treatment, n (%) | 2 (6.9%) | 0 (0) |
| Total AEs[b] | 93 | 52 |
| Total SAEs | 21 | 2 |
| Total AEs leading to discontinuation of study treatment | 2 | 2 |
| Total severe AEs | 27 | 4 |
| Total AEs suspected to be related to study treatment | 4 | 0 |
| Total SAEs or AEs leading to discontinuation of study treatment suspected to be related to study treatment | 0 | 0 |

[a]Subjects may fall into more than one category.
[b]Events are counted by dictionary-derived term. Events that were reported more than once in a given subject are counted only once.

The most frequently reported AEs were hypokalemia and pneumothorax for the placebo group and bradycardia and hypotension for the nitric oxide group. All AEs are presented in Table 14. Adverse events that occurred in 3 or more subjects in either treatment group are summarized in Table 13.

TABLE 13

Adverse Events Occurring in Three or More Subjects in Either Treatment Group by Actual Treatment Received

| Body System | AE (Coded Term) | Placebo[a] n = 29 | Nitric Oxide[a] 5 ppm n = 26 |
|---|---|---|---|
| Metabolism and nutrition disorders | Hypokalemia, n (%) | 6 (20.7%) | 2 (7.7%) |
| Cardiac disorders | Bradycardia, n (%) | 2 (6.9%) | 3 (11.5%) |
| Respiratory, thoracic and mediastinal disorders | Pneumothorax, n (%) | 3 (10.3%) | 2 (7.7%) |
| Vascular disorders | Hypotension, n (%) | 1 (3.4%) | 3 (11.5%) |

[a]Subjects with multiple occurrences of the same event are counted only once.

TABLE 14

Adverse Events by Actual Treatment Received

| Body System | Coded Term | Placebo[a] | Nitric Oxide 5 ppm[a] |
|---|---|---|---|
| Blood and lymphatic system disorders | Anemia | 1 (3.4%) | 1 (3.8%) |
| | Disseminated intravascular coagulation | 1 (3.4%) | 0 (0.0) |
| | Hemoglobinemia | 0 (0.0) | 1 (3.8%) |
| | Hemolytic anemia | 1 (3.4%) | 0 (0.0) |
| | Leukocytosis | 1 (3.4%) | 1 (3.8%) |
| | Thrombocythemia | 2 (6.9%) | 1 (3.8%) |
| | Thrombocytopenia | 1 (3.4%) | 0 (0.0) |
| Cardiac disorders | Arrhythmia | 0 (0.0) | 1 (3.8%) |
| | Bradycardia | 2 (6.9%) | 3 (11.5%) |
| | Cardiac arrest | 1 (3.4%) | 0 (0.0) |
| Eye disorders | Ocular icterus | 1 (3.4%) | 0 (0.0) |
| Gastrointestinal disorders | Abdominal distension | 1 (3.4%) | 0 (0.0) |
| | Ascites | 0 (0.0) | 1 (3.8%) |
| | Diarrhea | 1 (3.4%) | 0 (0.0) |
| | Gastrointestinal hemorrhage | 1 (3.4%) | 0 (0.0) |
| | Pancreatitis | 2 (6.9%) | 0 (0.0) |
| General disorders and administration site conditions | Generalized edema | 1 (3.4%) | 0 (0.0) |
| | Hypothermia | 1 (3.4%) | 0 (0.0) |
| | Multi-organ failure | 2 (6.9%) | 0 (0.0) |
| | Pyrexia | 2 (6.9%) | 0 (0.0) |
| | Unevaluable event | 1 (3.4%) | 2 (7.7%) |
| Hepatobiliary disorders | Hepatic failure | 1 (3.4%) | 0 (0.0) |
| | Hepatosplenomegaly | 0 (0.0) | 1 (3.8%) |
| Infections and infestations | Bacteremia | 0 (0.0) | 2 (7.7%) |
| | Empyema | 1 (3.4%) | 0 (0.0) |
| | Fungemia | 0 (0.0) | 1 (3.8%) |
| | Gangrene | 0 (0.0) | 1 (3.8%) |
| | Lung infection, pseudomonal | 1 (3.4%) | 0 (0.0) |
| | Pneumonia | 0 (0.0) | 1 (3.8%) |
| | Pneumonia, *aspergillus* | 1 (3.4%) | 0 (0.0) |
| | Pneumonia, staphylococcal | 1 (3.4%) | 1 (3.8%) |
| | Pseudomonal sepsis | 0 (0.0) | 1 (3.8%) |
| | Sepsis | 1 (3.4%) | 0 (0.0) |
| | Tracheitis | 0 (0.0) | 2 (7.7%) |
| | Urinary tract infection | 1 (3.4%) | 1 (3.8%) |
| | Urinary tract infection, fungal | 0 (0.0) | 1 (3.8%) |

TABLE 14-continued

Adverse Events by Actual Treatment Received

| Body System | Coded Term | Placebo[a] | Nitric Oxide 5 ppm[a] |
|---|---|---|---|
| Injury, poisoning and procedural complications | Device failure | 1 (3.4%) | 0 (0.0) |
| | Hemothorax | 1 (3.4%) | 0 (0.0) |
| | Skin injury | 1 (3.4%) | 0 (0.0) |
| | Subdural hematoma | 1 (3.4%) | 0 (0.0) |
| Investigations | Bacteria, blood | 1 (3.4%) | 1 (3.8%) |
| | Bacteria, sputum | 2 (6.9%) | 0 (0.0) |
| | Bronchoalveolar lavage | 1 (3.4%) | 1 (3.8%) |
| | C-reactive protein increased | 1 (3.4%) | 0 (0.0) |
| | Fungus culture positive | 2 (6.9%) | 0 (0.0) |
| Investigations (continued) | Fungus urine test positive | 1 (3.4%) | 0 (0.0) |
| | Oxygen saturation decreased | 1 (3.4%) | 2 (7.7%) |
| | Urine output decreased | 1 (3.4%) | 1 (3.8%) |
| | White blood cell count increased | 1 (3.4%) | 0 (0.0) |
| Metabolism and nutrition disorders | Acidosis | 0 (0.0) | 1 (3.8%) |
| | Diabetic ketoacidosis | 1 (3.4%) | 0 (0.0) |
| | Feeding disorder | 1 (3.4%) | 0 (0.0) |
| | Hyperammonemia | 1 (3.4%) | 0 (0.0) |
| | Hypercalcemia | 1 (3.4%) | 1 (3.8%) |
| | Hyperchloremia | 0 (0.0) | 1 (3.8%) |
| | Hyperglycemia | 0 (0.0) | 1 (3.8%) |
| | Hyperkalemia | 2 (6.9%) | 1 (3.8%) |
| | Hyperlipidemia | 1 (3.4%) | 0 (0.0) |
| | Hypernatremia | 0 (0.0) | 2 (7.7%) |
| | Hypocalcemia | 0 (0.0) | 1 (3.8%) |
| | Hypochloremia | 1 (3.4%) | 0 (0.0) |
| | Hypokalemia | 6 (20.7%) | 2 (7.7%) |
| | Metabolic acidosis | 1 (3.4%) | 0 (0.0) |
| | Metabolic alkalosis | 1 (3.4%) | 1 (3.8%) |
| Nervous system disorders | Brain edema | 1 (3.4%) | 0 (0.0) |
| | Cerebral artery occlusion | 1 (3.4%) | 0 (0.0) |
| | Intracranial pressure increased | 1 (3.4%) | 0 (0.0) |
| Psychiatric disorders | Agitation | 2 (6.9%) | 2 (7.7%) |
| Renal and urinary disorders | Bladder distension | 1 (3.4%) | 0 (0.0) |
| | Hematuria | 1 (3.4%) | 0 (0.0) |
| | Oliguria | 1 (3.4%) | 0 (0.0) |
| | Renal failure | 2 (6.9%) | 1 (3.8%) |
| | Renal failure, acute | 1 (3.4%) | 0 (0.0) |
| | Renal impairment | 1 (3.4%) | 0 (0.0) |
| Respiratory, thoracic and mediastinal disorders | Apnea | 0 (0.0) | 1 (3.8%) |
| | Hemopneumothorax | 1 (3.4%) | 0 (0.0) |
| | Hypercapnia | 1 (3.4%) | 0 (0.0) |
| | Hypoxia | 1 (3.4%) | 0 (0.0) |
| | Pleural effusion | 1 (3.4%) | 0 (0.0) |
| | Pneumomediastinum | 1 (3.4%) | 0 (0.0) |
| | Pneumothorax | 3 (10.3%) | 2 (7.7%) |
| | Pulmonary hemorrhage | 2 (6.9%) | 0 (0.0) |
| | Pulmonary hypertension | 1 (3.4%) | 0 (0.0) |
| | Respiratory acidosis | 1 (3.4%) | 0 (0.0) |
| | Respiratory failure | | |
| Skin and subcutaneous tissue disorders | Pruritus | 1 (3.4%) | 0 (0.0) |
| Surgical and medical procedures | Chest tube insertion | 0 (0.0) | 1 (3.8%) |
| | Medical device removal | 1 (3.4%) | 0 (0.0) |
| Vascular disorders | Deep vein thrombosis | 0 (0.0) | 2 (7.7%) |
| | Hemorrhage | 1 (3.4%) | 0 (0.0) |
| Vascular disorders (continued) | Hypertension | 2 (6.9%) | 0 (0.0) |
| | Hypotension | 1 (3.4%) | 3 (11.5%) |
| | Labile blood pressure | 1 (3.4%) | 0 (0.0) |

[a]Subjects with multiple occurrences of the same event are counted only once.

Four AEs, reported in 2 subjects in the placebo group, were suspected to be related to study treatment (one subject had agitation and hyperlipidemia; another subject had hyperammonemia and increased C-reactive protein). All of these were non-serious AEs that were mild, and all but hyperammonemia had resolved by the end of the study (see Table 15).

TABLE 15

Adverse Events by Actual Treatment Received and by Relationship to Study Treatment

| Body System | Coded Term | Not Suspected[a] | | Suspected[a] | |
| --- | --- | --- | --- | --- | --- |
| | | Placebo | Nitric Oxide 5 ppm | Placebo | Nitric Oxide 5 ppm |
| Blood and lymphatic system disorders | Anemia | 1 (3.4%) | 1 (3.8%) | 0 (0.0) | 0 (0.0) |
| | Disseminated intravascular coagulation | 1 (3.4%) | 0 (0.0) | 0 (0.0) | 0 (0.0) |
| | Hemoglobinemia | 0 (0.0) | 1 (3.8%) | 0 (0.0) | 0 (0.0) |
| | Hemolytic anemia | 1 (3.4%) | 0 (0.0) | 0 (0.0) | 0 (0.0) |
| | Leukocytosis | 1 (3.4%) | 1 (3.8%) | 0 (0.0) | 0 (0.0) |
| | Thrombocythemia | 2 (6.9%) | 1 (3.8%) | 0 (0.0) | 0 (0.0) |
| | Thrombocytopenia | 1 (3.4%) | 0 (0.0) | 0 (0.0) | 0 (0.0) |
| Cardiac disorders | Arrhythmia | 0 (0.0) | 1 (3.8%) | 0 (0.0) | 0 (0.0) |
| | Bradycardia | 2 (6.9%) | 3 (11.5%) | 0 (0.0) | 0 (0.0) |
| | Cardiac arrest | 1 (3.4%) | 0 (0.0) | 0 (0.0) | 0 (0.0) |
| Eye disorders | Ocular icterus | 1 (3.4%) | 0 (0.0) | 0 (0.0) | 0 (0.0) |
| Gastrointestinal disorders | Abdominal distension | 1 (3.4%) | 0 (0.0) | 0 (0.0) | 0 (0.0) |
| | Ascites | 0 (0.0) | 1 (3.8%) | 0 (0.0) | 0 (0.0) |
| | Diarrhea | 1 (3.4%) | 0 (0.0) | 0 (0.0) | 0 (0.0) |
| | Gastrointestinal hemorrhage | 1 (3.4%) | 0 (0.0) | 0 (0.0) | 0 (0.0) |
| | Pancreatitis | 2 (6.9%) | 0 (0.0) | 0 (0.0) | 0 (0.0) |
| General disorders and administration site conditions | Generalized edema | 1 (3.4%) | 0 (0.0) | 0 (0.0) | 0 (0.0) |
| | Hypothermia | 1 (3.4%) | 0 (0.0) | 0 (0.0) | 0 (0.0) |
| | Multi-organ failure | 2 (6.9%) | 0 (0.0) | 0 (0.0) | 0 (0.0) |
| | Pyrexia | 2 (6.9%) | 0 (0.0) | 0 (0.0) | 0 (0.0) |
| | Unevaluable event | 1 (3.4%) | 2 (7.7%) | 0 (0.0) | 0 (0.0) |
| Hepatobiliary disorders | Hepatic failure | 1 (3.4%) | 0 (0.0) | 0 (0.0) | 0 (0.0) |
| | Hepatosplenomegaly | 0 (0.0) | 1 (3.8%) | 0 (0.0) | 0 (0.0) |
| Infections and infestations | Bacteremia | 0 (0.0) | 2 (7.7%) | 0 (0.0) | 0 (0.0) |
| | Empyema | 1 (3.4%) | 0 (0.0) | 0 (0.0) | 0 (0.0) |
| | Fungemia | 0 (0.0) | 1 (3.8%) | 0 (0.0) | 0 (0.0) |
| | Grangrene | 0 (0.0) | 1 (3.8%) | 0 (0.0) | 0 (0.0) |
| | Lung infection, pseudomonal | 1 (3.4%) | 0 (0.0) | 0 (0.0) | 0 (0.0) |
| | Pneumonia | 0 (0.0) | 1 (3.8%) | 0 (0.0) | 0 (0.0) |
| | Pneumonia, *aspergillus* | 1 (3.4%) | 0 (0.0) | 0 (0.0) | 0 (0.0) |
| | Pneumonia, staphylococcal | 1 (3.4%) | 1 (3.8%) | 0 (0.0) | 0 (0.0) |
| | Pseudomonal sepsis | 0 (0.0) | 1 (3.8%) | 0 (0.0) | 0 (0.0) |
| | Sepsis | 1 (3.4%) | 0 (0.0) | 0 (0.0) | 0 (0.0) |
| | Tracheitis | 0 (0.0) | 2 (7.7%) | 0 (0.0) | 0 (0.0) |
| | Urinary tract infection | 1 (3.4%) | 1 (3.8%) | 0 (0.0) | 0 (0.0) |
| | Urinary tract infection, fungal | 0 (0.0) | 1 (3.8%) | 0 (0.0) | 0 (0.0) |
| Injury, poisoning and procedural complications | Device failure | 1 (3.4%) | 0 (0.0) | 0 (0.0) | 0 (0.0) |
| | Hemothorax | 1 (3.4%) | 0 (0.0) | 0 (0.0) | 0 (0.0) |
| | Skin injury | 1 (3.4%) | 0 (0.0) | 0 (0.0) | 0 (0.0) |
| | Subdural hematoma | 1 (3.4%) | 0 (0.0) | 0 (0.0) | 0 (0.0) |
| Investigations | Bacteria, blood | 1 (3.4%) | 1 (3.8%) | 0 (0.0) | 0 (0.0) |
| | Bacteria, sputum | 2 (6.9%) | 0 (0.0) | 0 (0.0) | 0 (0.0) |
| | Bronchoalveolar lavage | 1 (3.4%) | 1 (3.8%) | 0 (0.0) | 0 (0.0) |
| | C-reactive protein increased | 0 (0.0) | 0 (0.0) | 1 (3.4%) | 0 (0.0) |
| | Fungus culture positive | 2 (6.9%) | 0 (0.0) | 0 (0.0) | 0 (0.0) |
| | Fungus urine test positive | 1 (3.4%) | 0 (0.0) | 0 (0.0) | 0 (0.0) |
| | Oxygen saturation decreased | 1 (3.4%) | 2 (7.7%) | 0 (0.0) | 0 (0.0) |
| | Urine output decreased | 1 (3.4%) | 1 (3.8%) | 0 (0.0) | 0 (0.0) |
| | White blood cell count increased | 1 (3.4%) | 0 (0.0) | 0 (0.0) | 0 (0.0) |
| Metabolism and nutrition disorders | Acidosis | 0 (0.0) | 1 (3.8%) | 0 (0.0) | 0 (0.0) |
| | Diabetic ketoacidosis | 1 (3.4%) | 0 (0.0) | 0 (0.0) | 0 (0.0) |
| | Feeding disorder | 1 (3.4%) | 0 (0.0) | 0 (0.0) | 0 (0.0) |
| | Hyperammonemia | 0 (0.0) | 0 (0.0) | 1 (3.4%) | 0 (0.0) |
| | Hypercalcemia | 1 (3.4%) | 1 (3.8%) | 0 (0.0) | 0 (0.0) |
| | Hyperchloremia | 0 (0.0) | 1 (3.8%) | 0 (0.0) | 0 (0.0) |
| | Hyperglycemia | 0 (0.0) | 1 (3.8%) | 0 (0.0) | 0 (0.0) |
| | Hyperkalemia | 2 (6.9%) | 1 (3.8%) | 0 (0.0) | 0 (0.0) |
| | Hyperlipidemia | 0 (0.0) | 0 (0.0) | 1 (3.4%) | 0 (0.0) |
| | Hypernatremia | 0 (0.0) | 2 (7.7%) | 0 (0.0) | 0 (0.0) |

TABLE 15-continued

Adverse Events by Actual Treatment Received and by Relationship to Study Treatment

| | | Not Suspected[a] | | Suspected[a] | |
|---|---|---|---|---|---|
| Body System | Coded Term | Placebo | Nitric Oxide 5 ppm | Placebo | Nitric Oxide 5 ppm |
| Metabolism and nutrition disorders (continued) | Hypocalcemia | 0 (0.0) | 1 (3.8%) | 0 (0.0) | 0 (0.0) |
| | Hypochloremia | 1 (3.4%)) | 0 (0.0) | 0 (0.0) | 0 (0.0) |
| | Hypokalemia | 6 (20.7%) | 2 (7.7%) | 0 (0.0) | 0 (0.0) |
| | Metabolic acidosis | 1 (3.4%) | 0 (0.0) | 0 (0.0) | 0 (0.0) |
| | Metabolic alkalosis | 1 (3.4%) | 1 (3.8%) | 0 (0.0) | 0 (0.0) |
| Nervous system disorders | Brain edema | 1 (3.4%) | 0 (0.0) | 0 (0.0) | 0 (0.0) |
| | Cerebral artery occlusion | 1 (3.4%) | 0 (0.0) | 0 (0.0) | 0 (0.0) |
| | Intracranial pressure increased | 1 (3.4%) | 0 (0.0) | 0 (0.0) | 0 (0.0) |
| Psychiatric disorders | Agitation | 1 (3.4%) | 2 (7.7%) | 1 (3.4%) | 0 (0.0) |
| Renal and urinary disorders | Bladder distension | 1 (3.4%) | 0 (0.0) | 0 (0.0) | 0 (0.0) |
| | Hematuria | 1 (3.4%) | 0 (0.0) | 0 (0.0) | 0 (0.0) |
| | Oliguria | 1 (3.4%) | 0 (0.0) | 0 (0.0) | 0 (0.0) |
| | Renal failure | 2 (6.9%) | 1 (3.8%) | 0 (0.0) | 0 (0.0) |
| | Renal failure, acute | 1 (3.4%) | 0 (0.0) | 0 (0.0) | 0 (0.0) |
| | Renal impairment | 1 (3.4%) | 0 (0.0) | 0 (0.0) | 0 (0.0) |
| Respiratory, thoracic and mediastinal disorders | Apnea | 0 (0.0) | 1 (3.8%) | 0 (0.0) | 0 (0.0) |
| | Hemopneumothorax | 1 (3.4%) | 0 (0.0) | 0 (0.0) | 0 (0.0) |
| | Hypercapnia | 1 (3.4%) | 0 (0.0) | 0 (0.0) | 0 (0.0) |
| | Hypoxia | 1 (3.4%) | 0 (0.0) | 0 (0.0) | 0 (0.0) |
| Respiratory, thoracic and mediastinal disorders (continued) | Pleural effusion | 1 (3.4%) | 0 (0.0) | 0 (0.0) | 0 (0.0) |
| | Pneumomediastinum | 1 (3.4%) | 0 (0.0) | 0 (0.0) | 0 (0.0) |
| | Pneumothorax | 3 (10.3%) | 2 (7.7%) | 0 (0.0) | 0 (0.0) |
| | Pulmonary hemorrhage | 2 (6.9%) | 0 (0.0) | 0 (0.0) | 0 (0.0) |
| | Pulmonary hypertension | 1 (3.4%) | 0 (0.0) | 0 (0.0) | 0 (0.0) |
| | Respiratory acidosis | 1 (3.4%) | 0 (0.0) | 0 (0.0) | 0 (0.0) |
| | Respiratory failure | 1 (3.4%) | 1 (3.8%) | 0 (0.0) | 0 (0.0) |
| Skin and subcutaneous tissue disorders | Pruritus | 1 (3.4%) | 0 (0.0) | 0 (0.0) | 0 (0.0) |
| Surgical and medical procedures | Chest tube insertion | 0 (0.0) | 1 (3.8%) | 0 (0.0) | 0 (0.0) |
| | Medical device removal | 1 (3.4%) | 0 (0.0) | 0 (0.0) | 0 (0.0) |
| Vascular disorders | Deep vein thrombosis | 0 (0.0) | 2 (7.7%) | 0 (0.0) | 0 (0.0) |
| | Hemorrhage | 1 (3.4%) | 0 (0.0) | 0 (0.0) | 0 (0.0) |
| | Hypertension | 2 (6.9%) | 0 (0.0) | 0 (0.0) | 0 (0.0) |
| | Hypotension | 1 (3.4%) | 3 (11.5%) | 0 (0.0) | 0 (0.0) |
| | Labile blood pressure | 1 (3.4%) | 0 (0.0) | 0 (0.0) | 0 (0.0) |

[a]Subjects with multiple occurrences of the same event are counted only once.

Deaths, Other Serious Adverse Events, and Other Significant Adverse Events

Eleven subjects died during the study or follow-up period. Eight died during treatment with placebo, 2 died during treatment with nitric oxide, and 1 died during the follow-up period after treatment with nitric oxide. All subjects who died are identified in Table 16. Four subjects who died had no AE listed where "death" was the outcome, and 1 of these subjects died after the treatment period. A summary of AEs in which death was the outcome is provided in Table 17. None of the AEs in which death was the outcome was suspected of being related to the study treatment (Table 18).

TABLE 16

Identification of All Subjects Who Died

| Subject Number | Sex | Age (y) | AE[a] in Which Death was the Outcome |
|---|---|---|---|
| Placebo | | | |
| 1005 | F | 7.2 | Sepsis |
| 1006 | M | 11.4 | Cardiac arrest |
| 1011 | F | 13.8 | Brain edema, hemolytic anemia, hepatic failure, pancreatitis, renal failure, renal impairment, respiratory failure,[b] hypoxia[b] |
| 3007 | M | 1.7 | No AE listed in which death was the outcome |
| 3009 | M | 15.5 | No AE listed in which death was the outcome |
| 6001 | M | 11.5 | Diabetic ketoacidosis, multi-organ failure |
| 8003 | M | 14.7 | Intracranial pressure increased |
| 8004 | M | 2.9 | Pneumonia Aspergillus pulmonary hemorrhage |
| Nitric Oxide | | | |
| 2001A[c] | F | 1.5 | No AE listed in which death was the outcome |
| 2007 | F | 8.6 | No AE listed in which death was the outcome |
| 3003 | M | 3.2 | Bradycardia, hypotension |

[a]All AEs in which death was the outcome were SAEs.
[b]Death was not listed as the outcome of this SAE.
[c]The subject died after the treatment period.

TABLE 17

Adverse Events in Which Death was the Outcome by Actual Treatment Received

| Body System | Coded Term | Placebo[a] | Nitric Oxide 5 ppm[a] |
|---|---|---|---|
| Blood and lymphatic system disorders | Hemolytic anemia | 1 (3.4%) | 0 (0.0) |
| Cardiac disorders | Bradycardia | 0 (0.0) | 1 (3.8%) |
|  | Cardiac arrest | 1 (3.4%) | 0 (0.0) |
| Gastrointestinal disorders | Pancreatitis | 1 (3.4%) | 0 (0.0) |
| General disorders and administration site conditions | Multi-organ failure | 1 (3.4%) | 0 (0.0) |
| Hepatobiliary disorders | Hepatic failure | 1 (3.4%) | 0 (0.0) |
| Infections and infestations | Pneumonia, *aspergillus* | 1 (3.4%) | 0 (0.0) |
|  | Sepsis | 1 (3.4%) | 0 (0.0) |
| Metabolism and nutrition disorders | Diabetic ketoacidosis | 1 (3.4%) | 0 (0.0) |
| Nervous system disorders | Brain edema | 1 (3.4%) | 0 (0.0) |
|  | Intracranial pressure increased | 1 (3.4%) | 0 (0.0) |
| Renal and urinary disorders | Renal failure | 1 (3.4%) | 0 (0.0) |
|  | Renal impairment | 1 (3.4%) | 0 (0.0) |
| Respiratory, thoracic and mediastinal disorders | Pulmonary hemorrhage | 1 (3.4%) | 0 (0.0) |
| Vascular disorders | Hypotension | 0 (0.0) | 1 (3.8%) |

[a]Subjects with multiple occurrences of the same event are counted only once.

TABLE 18

Adverse Events in Which Death was the Outcome by Actual Treatment Received and by Relationship to Treatment

| Body System | Coded Term | Not Suspected[a] | | Suspected[a] | |
|---|---|---|---|---|---|
|  |  | Placebo | Nitric Oxide 5 ppm | Placebo | Nitric Oxide 5 ppm |
| Blood and lymphatic system disorders | Hemolytic anemia | 1 (3.4%) | 0 (0.0) | 0 (0.0) | 0 (0.0) |
| Cardiac disorders | Bradycardia | 0 (0.0) | 1 (3.8%) | 0 (0.0) | 0 (0.0) |
|  | Cardiac arrest | 1 (3.4%) | 0 (0.0) | 0 (0.0) | 0 (0.0) |
| Gastrointestinal disorders | Pancreatitis | 1 (3.4%) | 0 (0.0) | 0 (0.0) | 0 (0.0) |
| General disorders and administration site conditions | Multi-organ failure | 1 (3.4%) | 0 (0.0) | 0 (0.0) | 0 (0.0) |
| Hepatobiliary disorders | Hepatic failure | 1 (3.4%) | 0 (0.0) | 0 (0.0) | 0 (0.0) |
| Infections and infestations | Pneumonia, *aspergillus* | 1 (3.4%) | 0 (0.0) | 0 (0.0) | 0 (0.0) |
|  | Sepsis | 1 (3.4%) | 0 (0.0) | 0 (0.0) | 0 (0.0) |
| Metabolism and nutrition disorders | Diabetic ketoacidosis | 1 (3.4%) | 0 (0.0) | 0 (0.0) | 0 (0.0) |
| Nervous system disorders | Brain edema | 1 (3.4%) | 0 (0.0) | 0 (0.0) | 0 (0.0) |
|  | Intracranial pressure increased | 1 (3.4%) | 0 (0.0) | 0 (0.0) | 0 (0.0) |
| Renal and urinary disorders | Renal failure | 1 (3.4%) | 0 (0.0) | 0 (0.0) | 0 (0.0) |
|  | Renal impairment | 1 (3.4%) | 0 (0.0) | 0 (0.0) | 0 (0.0) |
| Repiratory, thoracic and mediastinal disorders | Pulmonary hemorrhage | 1 (3.4%) | 0 (0.0) | 0 (0.0) | 0 (0.0) |
| Vascular disorders | Hypotension | 0 (0.0) | 1 (3.8%) | 0 (0.0) | 0 (0.0) |

[a]Subjects with multiple occurrences of the same event are counted only once.

There were 21 SAEs reported in 8 of the 29 subjects who received placebo (27.6%) and 2 SAEs reported in 1 of the 26 subjects who received nitric oxide (3.9%). All subjects with SAEs are identified in Table 19. No SAE was reported by more than 1 subject in either treatment group (Table 20), and no SAE had a suspected relationship to study treatment (Table 21).

TABLE 19

Identification of All Subjects with Serious Adverse Events

| Subject Number | Sex | Age (y) | SAE | Action/Reported Outcome |
|---|---|---|---|---|
| Placebo |  |  |  |  |
| 1005 | F | 7.2 | Sepsis | DC/death |
| 1006 | M | 11.4 | Cardiac arrest | Con med/death |
| 1011 | F | 13.8 | Brain edema, hemolytic anemia, hepatic failure, pancreatits, renal failure, renal impairment | Con med/death |
|  |  |  | Respiratory failure, hypoxia | Extended hospitalization/ improved |
| 3007 | M | 1.7 | Subdural hematoma | Surgical intervention/ recovered |
| 3008 | M | 4.2 | Hemothorax, unevaluable event (severe respiratory air-leak syndrome), renal failure acute | Surgical intervention/ recovered |
|  |  |  | Cerebral artery occlusion | Surgical |

TABLE 19-continued

Identification of All Subjects with Serious Adverse Events

| Subject Number | Sex | Age (y) | SAE | Action/Reported Outcome |
|---|---|---|---|---|
| 6001 | M | 11.5 | Diabetic ketoacidosis, multi-organ failure | intervention/improved No action/death |
| | | | Hemopneumothorax | Surgical intervention/improved |
| 8003 | M | 14.7 | Intracranial pressure increased | Con med/death |
| 8004 | M | 2.9 | Pulmonary hemorrhage | DC/death |
| | | | Pneumonia *Aspergillus* | Con med/death |

Nitric Oxide

| 3003 | M | 3.2 | Bradycardia, hypotension | DC/death |

Abbreviations:
DC = discontinued treatment;
Con med = concomitant medication taken

TABLE 20

Serious Adverse Events by Actual Treatment Received

| Body System | Coded Term | Placebo[a] | Nitric Oxide 5 ppm[a] |
|---|---|---|---|
| Blood and lymphatic system disorders | Hemolytic anemia | 1 (3.4%) | 0 (0.0) |
| Cardiac disorders | Bradycardia | 0 (0.0) | 1 (3.8%) |
| | Cardiac arrest | 1 (3.4%) | 0 (0.0) |
| Gastrointestinal disorders | Pancreatitis | 1 (3.4%) | 0 (0.0) |
| General disorders and administration site conditions | Multi-organ failure | 1 (3.4%) | 0 (0.0) |
| | Unevaluable event | 1 (3.4%) | 0 (0.0) |
| Hepatobiliary disorders | Hepatic failure | 1 (3.4%) | 0 (0.0) |
| Infections and infestations | Pneumonia, *aspergillus* | 1 (3.4%) | 0 (0.0) |
| | Sepsis | 1 (3.4%) | 0 (0.0) |
| Injury, poisoning and procedural complications | Hemothorax | 1 (3.4%) | 0 (0.0) |
| | Subdural hematoma | 1 (3.4%) | 0 (0.0) |
| Metabolism and nutrition disorders | Diabetic ketoacidosis | 1 (3.4%) | 0 (0.0) |
| Nervous system disorders | Brain edema | 1 (3.4%) | 0 (0.0) |
| | Cerebral artery occlusion | 1 (3.4%) | 0 (0.0) |
| | Intracranial pressure increased | 1 (3.4%) | 0 (0.0) |
| Renal and urinary disorders | Renal failure | 1 (3.4%) | 0 (0.0) |
| | Renal failure, acute | 1 (3.4%) | 0 (0.0) |
| | Renal impairment | 1 (3.4%) | 0 (0.0) |
| Respiratory, thoracic and mediastinal disorders | Hemopneumothorax | 1 (3.4%) | 0 (0.0) |
| | Hypoxia | 1 (3.4%) | 0 (0.0) |
| | Pulmonary hemorrhage | 1 (3.4%) | 0 (0.0) |
| | Respiratory failure | 1 (3.4%) | 0 (0.0) |
| Vascular disorders | Hypotension | 0 (0.0) | 1 (3.8%) |

[a]Subjects with multiple occurrences of the same event are counted only once.

TABLE 21

Serious Adverse Events by Actual Treatment Received and by Relationship to Study Treatment

| | | Not Suspected[a] | | Suspected[a] | |
|---|---|---|---|---|---|
| Body System | Coded Term | Placebo | Nitric Oxide 5 ppm | Placebo | Nitric Oxide 5 ppm |
| Blood and lymphatic system disorders | Hemolytic anemia | 1 (3.4%) | 0 (0.0) | 0 (0.0) | 0 (0.0) |
| Cardiac disorders | Bradycardia | 0 (0.0) | 1 (3.8%) | 0 (0.0) | 0 (0.0) |
| | Cardiac arrest | 1 (3.4%) | 0 (0.0) | 0 (0.0) | 0 (0.0) |
| Gastrointestinal disorders | Pancreatitis | 1 (3.4%) | 0 (0.0) | 0 (0.0) | 0 (0.0) |
| General disorders and administration site conditions | Multi-organ failure | 1 (3.4%) | 0 (0.0) | 0 (0.0) | 0 (0.0) |
| | Unevaluable event | 1 (3.4%) | 0 (0.0) | 0 (0.0) | 0 (0.0) |
| Hepatobiliary disorders | Hepatic failure | 1 (3.4%) | 0 (0.0) | 0 (0.0) | 0 (0.0) |
| Infections and infestations | Pneumonia, *aspergillus* | 1 (3.4%) | 0 (0.0) | 0 (0.0) | 0 (0.0) |
| | Sepsis | 1 (3.4%) | 0 (0.0) | 0 (0.0) | 0 (0.0) |
| Injury, poisoning and procedural complications | Hemothorax | 1 (3.4%) | 0 (0.0) | 0 (0.0) | 0 (0.0) |
| | Subdural hematoma | 1 (3.4%) | 0 (0.0) | 0 (0.0) | 0 (0.0) |
| Metabolism and nutrition disorders | Diabetic ketoacidosis | 1 (3.4%) | 0 (0.0) | 0 (0.0) | 0 (0.0) |
| Nervous system disorders | Brain edema | 1 (3.4%) | 0 (0.0) | 0 (0.0) | 0 (0.0) |
| | Cerebral artery occlusion | 1 (3.4%) | 0 (0.0) | 0 (0.0) | 0 (0.0) |
| | Intracranial pressure increased | 1 (3.4%) | 0 (0.0) | 0 (0.0) | 0 (0.0) |
| Renal and urinary disorders | Renal failure | 1 (3.4%) | 0 (0.0) | 0 (0.0) | 0 (0.0) |
| | Renal failure, acute | 1 (3.4%) | 0 (0.0) | 0 (0.0) | 0 (0.0) |
| | Renal impairment | 1 (3.4%) | 0 (0.0) | 0 (0.0) | 0 (0.0) |

TABLE 21-continued

Serious Adverse Events by Actual Treatment Received and by Relationship to Study Treatment

| | | Not Suspected[a] | | Suspected[a] | |
|---|---|---|---|---|---|
| Body System | Coded Term | Placebo | Nitric Oxide 5 ppm | Placebo | Nitric Oxide 5 ppm |
| Respiratory, thoracic and mediastinal disorders | Hemopneumothorax | 1 (3.4%) | 0 (0.0) | 0 (0.0) | 0 (0.0) |
| | Hypoxia | 1 (3.4%) | 0 (0.0) | 0 (0.0) | 0 (0.0) |
| | Pulmonary hemorrhage | 1 (3.4%) | 0 (0.0) | 0 (0.0) | 0 (0.0) |
| | Respiratory failure | 1 (3.4%) | 0 (0.0) | 0 (0.0) | 0 (0.0) |
| Vascular disorders | Hypotension | 0 (0.0) | 1 (3.8%) | 0 (0.0) | 0 (0.0) |

[a]Subjects with multiple occurrences of the same event are counted only once.

Two AEs reported in 2 of the 29 subjects who received placebo (6.9%) and 2 AEs reported in 1 of the 26 subjects who received nitric oxide (3.9%) resulted in discontinuation of study treatment. All subjects in whom study treatment was discontinued because of one or more AEs are identified in Table 22. No AE that resulted in treatment discontinuation was reported by more than 1 subject in either treatment group (Table 23), and none had a suspected relationship to study treatment (Table 24).

TABLE 22

Identification of All Subjects in Whom Study Treatment was Discontinued Because of One or More Adverse Events

| Subject Number | Sex | Age (y) | SAE | Action/Reported Outcome |
|---|---|---|---|---|
| Placebo | | | | |
| 1005 | F | 7.2 | Sepsis[a] | DC/death |
| 8004 | M | 2.9 | Pulmonary hemorrhage[a] | DC/death |
| Nitric Oxide | | | | |
| 3003 | M | 3.2 | Bradycardia[a], hypotension[a] | DC/death |

Abbreviations:
DC = discontinued treatment
[a]SAE

TABLE 23

Adverse Events Where Treatment was Stopped by Actual Treatment Received

| Body System | Coded Term | Placebo[a] | Nitric Oxide 5 ppm[a] |
|---|---|---|---|
| Cardiac disorders | Bradycardia | 0 (0.0) | 1 (3.8%) |
| Infections and infestations | Sepsis | 1 (3.4%) | 0 (0.0) |
| Respiratory, thoracic and mediastinal disorders | Pulmonary hemorrhage | 1 (3.4%) | 0 (00) |
| Vascular disorders | Hypotension | 0 (0.0) | 1 (3.8%) |

[a]Subjects with multiple occurrences of the same event are counted only once.

TABLE 24

Adverse Events Where Treatment was Stopped by Actual Study Treatment Received and by Relationship to Study Treatment

| | | Not Suspected[a] | | Suspected[a] | |
|---|---|---|---|---|---|
| Body System | Coded Term | Placebo | Nitric Oxide 5 ppm | Placebo | Nitric Oxide 5 ppm |
| Cardiac disorders | Bradycardia | 0 (0.0) | 1 (3.8%) | 0 (0.0) | 0 (0.0) |
| Infections and infestations | Sepsis | 1 (3.4%) | 0 (0.0) | 0 (0.0) | 0 (0.0) |
| Respiratory, thoracic and mediastinal disorders | Pulmonary hemorrhage | 1 (3.4%) | 0 (0.0) | 0 (0.0) | 0 (0.0) |
| Vascular disorders | Hypotension | 0 (0.0) | 1 (3.8%) | 0 (0.0) | 0 (0.0) |

[a]Subjects with multiple occurrences of the same event are counted only once.

Clinical Laboratory Evaluation

Percent methemoglobin levels were obtained at baseline and at Hours 4 and 24. The percent methemoglobin levels were within normal limits in both the placebo and the nitric oxide groups. These levels were well below levels that would have necessitated discontinuation of treatment. Percent methemoglobin levels are summarized in Table 25.

TABLE 25

Summary of Methemoglobin (%) Levels by Actual Treatment Received

| | Baseline | | 4 Hours | | 24 Hours | |
|---|---|---|---|---|---|---|
| | Placebo | Nitric Oxide 5 ppm | Placebo | Nitric Oxide 5 ppm | Placebo | Nitric Oxide 5 ppm |
| N | 22 | 22 | 27 | 25 | 24 | 23 |
| Mean (SD) | 0.63 (0.33) | 0.56 (0.35) | 0.67 (0.27) | 0.64 (0.33) | 0.52 (0.33) | 0.52 (0.37) |
| Median | 0.8 | 0.5 | 0.7 | 0.8 | 0.6 | 0.5 |
| Range | (0.0, 1.0) | (0.0, 1.0) | (0.0, 1.0) | (0.0, 1.0) | (0.0, 0.9) | (0.0, 1.0) |

Vital Signs, Physical Findings, and Other Observations Related to Safety

Mean systolic and diastolic blood pressure increased slightly from baseline in both groups at 24 hours. Descriptive statistics for systolic and diastolic blood pressure, which were taken both at baseline and at 24 hours, are summarized Table 26.

TABLE 26

Descriptive Statistics for Vital Signs by Actual Treatment Received

| Vital Sign Value | Placebo | Nitric Oxide 5 ppm |
|---|---|---|
| Baseline | | |
| Systolic BP (mmHg) | | |
| N | 29 | 25 |
| Mean (SD) | 93.4 (17.6) | 94.4 (17.4) |
| Median | 95.0 | 95.5 |
| Range | (52.0, 128.0) | (63.0, 123.0) |
| Diastolic BP (mmHg) | | |
| N | 29 | 26 |
| Mean (SD) | 48.5 (12.5) | 54.6 (11.6) |
| Median | 47.0 | 55.5 |
| Range | (21.0, 77.0) | (38.0, 73.0) |
| 24 Hours | | |
| Systolic BP (mmHg) | | |
| N | 28 | 24 |
| Mean (SD) | 95.9 (17.8) | 97.9 (21.7) |
| Median | 97.0 | 103.0 |
| Range | (69.0, 132.0) | (50.0, 136.0) |
| Diastolic BP (mmHg) | | |
| N | 28 | 24 |
| Mean (SD) | 52.5 (9.9) | 56.0 (12.7) |
| Median | 52.5 | 54.5 |
| Range | (30.0, 72.0) | (39.0, 90.0) |

Descriptive statistics for the PRISM III Worksheet values taken at baseline (systolic blood pressure, temperature, heart rate, pupil reactivity, Glasgow Coma Scale, pH, carbon dioxide pressure [$pCO_2$], total carbon dioxide, partial pressure of oxygen [$PaO_2$], glucose, potassium, blood urea nitrogen, creatinine, white blood cell count, platelet count, prothrombin time, and partial thromboplastin time) are summarized in Table 27.

TABLE 27

Baseline PRISM 3 Worksheet Statistics, by Actual Treatment Received

| | Placebo | Nitric Oxide 5 ppm |
|---|---|---|
| Systolic BP (mmHg) | | |
| N | 29 | 26 |
| Mean (SD) | 85.0 (27.0) | 82.8 (23.8) |
| Median | 81.0 | 77.5 |
| Range | (0.0, 137.0) | (51.0, 142.0) |
| Temperature (C.) | | |
| N | 29 | 26 |
| Mean (SD) | 37.8 (1.4) | 37.6 (1.5) |
| Median | 38.2 | 38.1 |
| Range | (34.6, 40.0) | (34.6, 40.0) |
| Heart rate (bpm) | | |
| N | 29 | 26 |
| Mean (SD) | 155.3 (37.5) | 157.9 (37.9) |
| Median | 164.0 | 160.0 |
| Range | (0.0, 199.0) | (74.0, 216.0) |
| Pupils | | |
| Both Reactive | 24 (82.8%) | 20 (76.9%) |
| 1 Fixed | 1 (3.4%) | 0 (0%) |
| Both Fixed | 4 (13.8%) | 2 (7.7%) |
| Glasgow Coma Scale | | |
| N | 19 | 15 |
| Mean (SD) | 8.1 (4.7) | 8.7 (4.4) |
| Median | 8.0 | 9.0 |
| Range | (3.0, 15.0) | (3.0, 15.0) |
| pH (low) | | |
| N | 27 | 23 |
| Mean (SD) | 7.3 (0.1) | 7.3 (0.1) |
| Median | 7.3 | 7.3 |
| Range | (7.0, 7.5) | (7.0, 7.6) |
| pH (high) | | |
| N | 26 | 21 |
| Mean (SD) | 7.4 (0.1) | 7.4 (0.1) |
| Median | 7.4 | 7.4 |
| Range | (7.2, 7.6) | (7.2, 7.6) |
| $pCO_2$ (mmHg) | | |
| N | 28 | 26 |
| Mean (SD) | 60.4 (19.1) | 56.7 (19.3) |
| Median | 59.2 | 53.0 |
| Range | (34.1, 113.2) | (24.8, 102.0) |

TABLE 27-continued

Baseline PRISM 3 Worksheet Statistics, by Actual Treatment Received

|  | Placebo | Nitric Oxide 5 ppm |
|---|---|---|
| Total $CO_2$ low (mEq/L) | | |
| N | 27 | 22 |
| Mean (SD) | 25.6 (6.2) | 25.5 (5.6) |
| Median | 24.0 | 25.0 |
| Range | (14.0, 38.0) | (15.0, 36.0) |
| Total $CO_2$ high (mEq/L) | | |
| N | 23 | 18 |
| Mean (SD) | 28.6 (6.0) | 26.5 (4.5) |
| Median | 29.0 | 27.0 |
| Range | (18.0, 40.0) | (14.0, 32.0) |
| $PaO_2$ (mmHg) | | |
| N | 26 | 20 |
| Mean (SD) | 56.4 (12.7) | 60.2 (13.6) |
| Median | 55.5 | 55.0 |
| Range | (33.0, 77.0) | (45.0, 91.0) |
| Glucose (mg/dL) | | |
| N | 27 | 24 |
| Mean (SD) | 160.1 (75.0) | 165.8 (105.2) |
| Median | 136.0 | 139.0 |
| Range | (52.0, 328.0) | (78.0, 543.0) |
| Potassium (mEq/L) | | |
| N | 28 | 25 |
| Mean (SD) | 4.1 (0.9) | 4.0 (0.7) |
| Median | 4.1 | 3.9 |
| Range | (2.1, 6.2) | (2.6, 5.4) |
| BUN (mg/dL) | | |
| N | 27 | 23 |
| Mean (SD) | 14.9 (17.1) | 13.8 (14.4) |
| Median | 10.0 | 9.0 |
| Range | (4.0, 75.0) | (1.0, 67.0) |
| Creatinine (mg/dL) | | |
| N | 27 | 23 |
| Mean (SD) | 0.7 (0.8) | 0.6 (0.5) |
| Median | 0.5 | 0.4 |
| Range | (0.1, 4.0) | (0.2, 2.4) |
| White blood cell count (μL) | | |
| N | 23 | 19 |
| Mean (SD) | 1142.5 (5,418.7) | 11.1 (16.1) |
| Median | 11.3 | 7.5 |
| Range | (1.1, 26,000.0[a]) | (0.8, 75.8) |
| Platelet Count (μL) | | |
| N | 23 | 19 |
| Mean (SD) | 223.6 (114.2) | 209.5 (105.1) |
| Median | 225.0 | 237.0 |
| Range | (52.0, 534.0) | (2.0, 394.0) |
| Prothrombin Time (s) | | |
| N | 17 | 10 |
| Mean (SD) | 17.5 (7.0) | 15.1 (6.1) |
| Median | 16.3 | 15.3 |
| Range | (1.2, 30.1) | (1.4, 26.5) |
| Partial Thromboplastin Time (s) | | |
| N | 17 | 10 |
| Mean (SD) | 45.8 (40.7) | 39.9 (9.3) |
| Median | 32.2 | 37.2 |
| Range | (22.8, 197.3) | (29.9, 61.1) |

Abbreviations:
BUN = blood urea nitrogen;
$pCO_2$ = carbon dioxide pressure;
$PaO_2$ = partial pressure of oxygen
[a] High white blood cell count value verified on case report form Descriptive statistics for the respiratory values are summarized in Table 28. Oxygen status was determined at screening only. Respiratory values in the HFOV category were obtained at baseline, 4 hours, 12 hours, and 24 hours. Respiratory values in the categories conventional mechanical ventilation [CMV] and ABG were obtained at baseline, 4 hours, 12 hours, 24 hours, and at extubation.

Of 6 subjects in whom a chest x-ray was performed, 4 (13.8%), all of whom were in the placebo group, had evidence of chronic changes/persistent infiltrates.

TABLE 28

Descriptive Statistics for Respiratory Values by Actual Treatment Received

|  |  | Placebo | Nitric oxide 5 ppm |
|---|---|---|---|
| Screening | | | |
| Oxygen Status | Oxygen Index 1 | | |
|  | N | 28 | 26 |
|  | Mean (SD) | 26.9 (15.0) | 22.2 (8.2) |
|  | Median | 25.4 | 21.3 |
|  | Range | (12.0, 90.9) | (12.4, 44.2) |
|  | Oxygen Index 2 | | |
|  | N | 29 | 26 |
|  | Mean (SD) | 27.1 (15.4) | 22.7 (7.9) |
|  | Median | 23.8 | 23.0 |
|  | Range | (13.4, 82.9) | (12.6, 40.0) |
| Baseline | | | |
| CMV | Rate (/min) | | |
|  | N | 20 | 19 |
|  | Mean (SD) | 26.1 (5.9) | 27.1 (6.6) |
|  | Median | 24.0 | 28.0 |
|  | Range | (16.0, 36.0) | (15.0, 40.0) |
|  | Pplat (cmH$_2$O) | | |
|  | N | 6 | 3 |
|  | Mean (SD) | 32.0 (3.3) | 28.7 (1.5) |
|  | Median | 33.0 | 29.0 |
|  | Range | (27.0, 36.0) | (27.0, 30.0) |
|  | PEEP (cmH$_2$O) | | |
|  | N | 20 | 19 |
|  | Mean (SD) | 10.9 (2.8) | 10.6 (2.9) |
|  | Median | 10.0 | 10.0 |
|  | Range | (7.0, 18.0) | (5.0, 16.0) |
|  | FiO$_2$ (%) | | |
|  | N | 20 | 19 |
|  | Mean (SD) | 71.0 (22.8) | 83.5 (20.3) |
|  | Median | 70.0 | 90.0 |
|  | Range | (1.0, 100.0) | (40.0, 100.0) |

TABLE 28-continued

Descriptive Statistics for Respiratory Values by Actual Treatment Received

| | | Placebo | Nitric oxide 5 ppm |
|---|---|---|---|
| Baseline CMV (continued) | MAP (cmH$_2$O) | | |
| | N | 20 | 19 |
| | Mean (SD) | 20.1 (5.6) | 17.8 (3.7) |
| | Median | 18.5 | 18.0 |
| | Range | (11.0, 34.0) | (11.8, 24.0) |
| | Set Vt (mL) | | |
| | N | 14 | 12 |
| | Mean (SD) | 186.5 (156.2) | 129.3 (74.3) |
| | Median | 127.5 | 110.0 |
| | Range | (40.0, 550.0) | (69.0, 348.0) |
| | Inspiratory time (s) | | |
| | N | 20 | 19 |
| | Mean (SD) | 0.9 (0.3) | 0.8 (0.3) |
| | Median | 0.9 | 0.8 |
| | Range | (0.5, 1.5) | (0.5, 1.5) |
| HFOV | Hertz (min) | | |
| | N | 9 | 7 |
| | Mean (SD) | 7.0 (2.3) | 7.7 (1.4) |
| | Median | 8.0 | 7.0 |
| | Range | (4.0, 10.0) | (6.0, 10.0) |
| | MAP (cmH$_2$O) | | |
| | N | 9 | 7 |
| | Mean (SD) | 27.7 (4.5) | 26.3 (2.6) |
| | Median | 26.0 | 26.4 |
| | Range | (23.0, 34.8) | (22.0, 30.0) |
| Baseline HFOV (continued) | Inspiratory Time (s) | | |
| | N | 9 | 7 |
| | Mean (SD) | 7.6 (14.4) | 5.0 (12.4) |
| | Median | 0.3 | 0.3 |
| | Range | (0.3, 33.0) | (0.0, 33.0) |
| | FiO$_2$ (%) | | |
| | N | 9 | 7 |
| | Mean (SD) | 92.6 (10.6) | 53.6 (22.4) |
| | Median | 100.0 | 40.0 |
| | Range | (75.0, 100.0) | (35.0, 95.0) |
| | delta P (cmH$_2$O) | | |
| | N | 9 | 6 |
| | Mean (SD) | 48.3 (14.3) | 47.2 (11.2) |
| | Median | 43.0 | 46.0 |
| | Range | (37.0, 81.0) | (35.0, 60.0) |
| ABG | pH | | |
| | N | 29 | 25 |
| | Mean (SD) | 7.4 (0.1) | 7.4 (0.1) |
| | Median | 7.4 | 7.4 |
| | Range | (7.1, 7.5) | (7.2, 7.6) |
| | PaO$_2$ (mmHg) | | |
| | N | 29 | 25 |
| | Mean (SD) | 72.4 (23.3) | 67.5 (13.1) |
| | Median | 66.0 | 63.0 |
| | Range | (41.0, 150.8) | (45.0, 97.0) |
| Baseline ABG (continued) | SaO$_2$ (%) | | |
| | N | 29 | 25 |
| | Mean (SD) | 92.1 (4.6) | 92.8 (3.5) |
| | Median | 93.0 | 92.0 |
| | Range | (81.0, 98.5) | (86.0, 100.0) |
| | PaCO$_2$ (mmHg) | | |
| | N | 29 | 25 |
| | Mean (SD) | 50.7 (15.0) | 45.3 (11.1) |
| | Median | 48.3 | 46.5 |
| | Range | (29.0, 101.0) | (25.2, 75.6) |
| | BE (mEq/L) | | |
| | N | 29 | 25 |
| | Mean (SD) | 1.9 (6.2) | 0.2 (5.3) |
| | Median | 1.4 | 0.4 |
| | Range | (−7.4, 13.0) | (−13.2, 11.0) |
| | HCO$_3$ (mEq/L) | | |
| | N | 29 | 25 |
| | Mean (SD) | 27.7 (5.8) | 25.6 (5.0) |
| | Median | 27.5 | 26.0 |
| | Range | (18.0, 38.3) | (14.6, 35.9) |
| 4 Hours | | | |
| CMV | Rate (/min) | | |
| | N | 21 | 18 |
| | Mean (SD) | 24.7 (6.7) | 25.5 (5.9) |
| | Median | 24.0 | 27.0 |
| | Range | (10.0, 36.0) | (15.0, 40.0) |
| CMV 4 Hours (continued) | Pplat (cmH$_2$O) | | |
| | N | 6 | 3 |
| | Mean (SD) | 29.5 (5.8) | 29.0 (2.0) |
| | Median | 30.0 | 29.0 |
| | Range | (23.0, 35.0) | (27.0, 31.0) |
| | PEEP (cmH$_2$O) | | |
| | N | 21 | 18 |
| | Mean (SD) | 11.2 (2.4) | 10.7 (3.2) |
| | Median | 10.0 | 10.5 |
| | Range | (7.0, 16.0) | (5.0, 18.0) |
| | FiO$_2$ (%) | | |
| | N | 21 | 18 |
| | Mean (SD) | 61.7 (22.9) | 63.9 (20.0) |
| | Median | 60.0 | 60.0 |
| | Range | (1.0, 100.0) | (35.0, 100.0) |
| | MAP (cmH$_2$O) | | |
| | N | 21 | 18 |
| | Mean (SD) | 19.1 (5.7) | 17.0 (3.5) |
| | Median | 19.0 | 17.5 |
| | Range | (12.0, 32.0) | (11.6, 24.0) |
| | Set Vt (mL) | | |
| | N | 14 | 11 |
| | Mean (SD) | 166.1 (154.3) | 131.3 (82.9) |
| | Median | 108.5 | 110.0 |
| | Range | (40.0, 520.0) | (65.0, 366.0) |
| CMV 4 Hours (continued) | Inspiratory Time (s) | | |
| | N | 21 | 18 |
| | Mean (SD) | 0.9 (0.3) | 0.8 (0.2) |
| | Median | 0.8 | 0.8 |
| | Range | (0.5, 1.5) | (0.5, 1.3) |
| HFOV | Hertz (min) | | |
| | N | 8 | 7 |
| | Mean (SD) | 7.1 (1.8) | 7.4 (1.9) |
| | Median | 7.5 | 7.0 |
| | Range | (4.4, 10.0) | (4.0, 10.0) |
| | MAP (cmH$_2$O) | | |
| | N | 8 | 7 |
| | Mean (SD) | 28.3 (5.8) | 26.6 (4.7) |
| | Median | 27.5 | 25.0 |
| | Range | (22.0, 38.0) | (21.0, 35.0) |
| | Inspiratory Time (s) | | |
| | N | 8 | 7 |
| | Mean (SD) | 8.5 (15.1) | 5.0 (12.4) |
| | Median | 0.3 | 0.3 |
| | Range | (0.0, 33.0) | (0.0, 33.0) |
| | FiO$_2$ (%) | | |
| | N | 8 | 7 |
| | Mean (SD) | 78.9 (23.5) | 52.9 (27.3) |
| | Median | 84.0 | 40.0 |
| | Range | (35.0, 100.0) | (25.0, 100.0) |
| HFOV 4 Hours (continued) | delta P (cmH$_2$O) | | |
| | N | 8 | 6 |
| | Mean (SD) | 46.9 (14.7) | 48.0 (15.5) |
| | Median | 44.0 | 45.5 |
| | Range | (33.0, 81.0) | (30.0, 72.0) |
| ABG 4 Hours | pH | | |
| | N | 28 | 22 |
| | Mean (SD) | 7.4 (0.1) | 7.4 (0.1) |
| | Median | 7.3 | 7.4 |
| | Range | (7.2, 7.6) | (7.0, 7.6) |
| | PaO$_2$ (mmHg) | | |
| | N | 28 | 22 |
| | Mean (SD) | 69.5 (26.9) | 83.2 (22.6) |
| | Median | 63.5 | 78.5 |
| | Range | (41.0, 177.0) | (57.0, 142.0) |
| | SaO$_2$ (%) | | |

TABLE 28-continued

Descriptive Statistics for Respiratory Values by Actual Treatment Received

| | | Placebo | Nitric oxide 5 ppm |
|---|---|---|---|
| ABG 4 Hours (continued) | N | 28 | 22 |
| | Mean (SD) | 90.7 (6.3) | 95.7 (2.9) |
| | Median | 92.5 | 95.9 |
| | Range | (72.0, 99.5) | (89.0, 100.0) |
| | $PaCO_2$ (mmHg) | | |
| | N | 28 | 22 |
| | Mean (SD) | 50.6 (12.3) | 46.0 (18.2) |
| | Median | 50.8 | 43.0 |
| | Range | (27.3, 73.0) | (33.0, 120.7) |
| | BE (mEq/L) | | |
| | N | 28 | 22 |
| | Mean (SD) | 2.1 (5.7) | 0.7 (4.1) |
| | Median | 2.0 | 1.0 |
| | Range | (−7.5, 14.0) | (−6.0, 7.6) |
| | $HCO_3$ (mEq/L) | | |
| | N | 28 | 22 |
| | Mean (SD) | 28.0 (5.6) | 25.7 (3.9) |
| | Median | 27.0 | 25.8 |
| | Range | (18.0, 39.0) | (19.0, 33.1) |
| 12 Hours | | | |
| CMV | Rate (/min) | | |
| | N | 20 | 17 |
| | Mean (SD) | 24.4 (6.6) | 24.5 (5.7) |
| | Median | 24.0 | 25.0 |
| | Range | (10.0, 36.0) | (15.0, 40.0) |
| | Pplat ($cmH_2O$) | | |
| | N | 6 | 4 |
| | Mean (SD) | 27.8 (7.2) | 25.8 (6.7) |
| | Median | 27.5 | 28.0 |
| | Range | (20.0, 36.0) | (16.0, 31.0) |
| | PEEP ($cmH_2O$) | | |
| | N | 20 | 17 |
| | Mean (SD) | 10.8 (3.6) | 10.6 (3.2) |
| | Median | 10.5 | 10.0 |
| | Range | (5.0, 22.0) | (5.0, 18.0) |
| CMV 12 Hours (continued) | $FiO_2$ (%) | | |
| | N | 20 | 17 |
| | Mean (SD) | 61.0 (22.2) | 59.0 (18.9) |
| | Median | 55.0 | 55.0 |
| | Range | (21.0, 100.0) | (36.0, 100.0) |
| | MAP ($cmH_2O$) | | |
| | N | 20 | 17 |
| | Mean (SD) | 18.0 (6.1) | 16.7 (3.8) |
| | Median | 17.0 | 18.0 |
| | Range | (11.0, 36.0) | (10.0, 24.0) |
| | Set Vt (mL) | | |
| | N | 12 | 13 |
| | Mean (SD) | 134.6 (116.5) | 126.5 (89.2) |
| | Median | 101.0 | 100.0 |
| | Range | (25.0, 380.0) | (70.0, 409.0) |
| | Inspiratory Time (s) | | |
| | N | 20 | 17 |
| | Mean (SD) | 0.9 (0.3) | 0.8 (0.2) |
| | Median | 0.8 | 0.8 |
| | Range | (0.5, 1.5) | (0.5, 1.3) |
| HFOV 12 Hours | Hertz (min) | | |
| | N | 9 | 8 |
| | Mean (SD) | 6.5 (1.8) | 7.9 (1.6) |
| | Median | 6.0 | 7.5 |
| | Range | (4.4, 10.0) | (6.0, 10.0) |
| HFOV 12 Hours (continued) | MAP ($cmH_2O$) | | |
| | N | 9 | 8 |
| | Mean (SD) | 28.7 (5.7) | 25.5 (5.2) |
| | Median | 29.0 | 23.9 |
| | Range | (22.0, 39.0) | (20.0, 36.0) |
| | Inspiratory Time (s) | | |
| | N | 9 | 8 |
| | Mean (SD) | 7.5 (14.4) | 4.4 (11.6) |
| | Median | 0.3 | 0.3 |
| | Range | (0.0, 33.0) | (0.0, 33.0) |
| | $FiO_2$ (%) | | |
| | N | 9 | 8 |
| | Mean (SD) | 60.3 (23.0) | 43.8 (16.0) |
| | Median | 58.0 | 42.5 |
| | Range | (30.0, 100.0) | (25.0, 70.0) |
| | delta P ($cmH_2O$) | | |
| | N | 9 | 7 |
| | Mean (SD) | 48.3 (14.1) | 46.1 (14.3) |
| | Median | 49.0 | 36.0 |
| | Range | (33.0, 82.0) | (34.0, 69.0) |
| ABG | pH | | |
| | N | 26 | 25 |
| | Mean (SD) | 7.4 (0.1) | 7.4 (0.1) |
| | Median | 7.4 | 7.4 |
| | Range | (7.1, 7.6) | (7.2, 7.5) |
| HFOV 12 Hours (continued) | MAP ($cmH_2O$) | | |
| | N | 9 | 8 |
| | Mean (SD) | 28.7 (5.7) | 25.5 (5.2) |
| | Median | 29.0 | 23.9 |
| | Range | (22.0, 39.0) | (20.0, 36.0) |
| | Inspiratory Time (s) | | |
| | N | 9 | 8 |
| | Mean (SD) | 7.5 (14.4) | 4.4 (11.6) |
| | Median | 0.3 | 0.3 |
| | Range | (0.0, 33.0) | (0.0, 33.0) |
| | $FiO_2$ (%) | | |
| | N | 9 | 8 |
| | Mean (SD) | 60.3 (23.0) | 43.8 (16.0) |
| | Median | 58.0 | 42.5 |
| | Range | (30.0, 100.0) | (25.0, 70.0) |
| | delta P ($cmH_2O$) | | |
| | N | 9 | 7 |
| | Mean (SD) | 48.3 (14.1) | 46.1 (14.3) |
| | Median | 49.0 | 36.0 |
| | Range | (33.0, 82.0) | (34.0, 69.0) |
| ABG | pH | | |
| | N | 26 | 25 |
| | Mean (SD) | 7.4 (0.1) | 7.4 (0.1) |
| | Median | 7.4 | 7.4 |
| | Range | (7.1, 7.6) | (7.2, 7.5) |
| ABG 12 Hours (continued) | $PaO_2$ (mmHg) | | |
| | N | 26 | 25 |
| | Mean (SD) | 72.1 (27.5) | 68.7 (20.9) |
| | Median | 64.5 | 68.0 |
| | Range | (29.0, 156.0) | (0.8, 118.0) |
| | $SaO_2$ (%) | | |
| | N | 26 | 25 |
| | Mean (SD) | 90.1 (10.3) | 93.1 (3.2) |
| | Median | 91.2 | 94.0 |
| | Range | (54.0, 99.5) | (84.0, 99.0) |
| | $PaCO_2$ (mmHg) | | |
| | N | 26 | 25 |
| | Mean (SD) | 51.1 (9.5) | 47.4 (8.3) |
| | Median | 50.7 | 48.4 |
| | Range | (31.0, 67.0) | (33.0, 68.0) |
| | BE (mEq/L) | | |
| | N | 26 | 25 |
| | Mean (SD) | 3.1 (5.7) | 1.1 (4.1) |
| | Median | 2.0 | 2.0 |
| | Range | (−4.5, 17.0) | (−6.5, 8.0) |
| | $HCO_2$ (mEq/L) | | |
| | N | 26 | 25 |
| | Mean (SD) | 28.9 (5.7) | 26.7 (4.1) |
| | Median | 28.0 | 27.0 |
| | Range | (21.0, 40.0) | (18.4, 35.9) |
| 24 Hours | | | |
| CMV | Rate (/min) | | |
| | N | 19 | 20 |
| | Mean (SD) | 23.4 (7.5) | 25.0 (6.6) |
| | Median | 22.0 | 25.5 |
| | Range | (10.0, 36.0) | (15.0, 40.0) |
| | Pplat ($cmH_2O$) | | |
| | N | 7 | 3 |
| | Mean (SD) | 29.3 (6.0) | 30.0 (4.6) |

TABLE 28-continued

Descriptive Statistics for Respiratory Values by Actual Treatment Received

| | | Placebo | Nitric oxide 5 ppm |
|---|---|---|---|
| | Median | 30.0 | 29.0 |
| | Range | (21.0, 38.0) | (26.0, 35.0) |
| | PEEP (cmH₂O) | | |
| | N | 19 | 20 |
| | Mean (SD) | 10.4 (3.8) | 9.8 (2.9) |
| | Median | 10.0 | 10.0 |
| | Range | (5.0, 22.0) | (5.0, 16.0) |
| | FiO₂ (%) | | |
| | N | 19 | 20 |
| | Mean (SD) | 56.9 (20.4) | 58.1 (16.6) |
| | Median | 55.0 | 55.0 |
| | Range | (21.0, 100.0) | (35.0, 100.0) |
| | MAP (cmH₂O) | | |
| | N | 19 | 20 |
| | Mean (SD) | 17.2 (5.5) | 16.0 (3.9) |
| | Median | 15.0 | 15.5 |
| | Range | (10.0, 30.0) | (10.0, 26.0) |
| CMV 24 Hours (continued) | Set Vt (mL) | | |
| | N | 13 | 11 |
| | Mean (SD) | 126.9 (114.0) | 123.3 (86.4) |
| | Median | 99.0 | 100.0 |
| | Range | (35.0, 380.0) | (60.0, 370.0) |
| | Inspiratory Time (s) | | |
| | N | 19 | 20 |
| | Mean (SD) | 0.9 (0.3) | 0.8 (0.2) |
| | Median | 0.8 | 0.8 |
| | Range | (0.5, 1.4) | (0.6, 1.1) |
| HFOV | Hertz (min) | | |
| | N | 9 | 5 |
| | Mean (SD) | 7.0 (1.9) | 8.3 (1.9) |
| | Median | 7.0 | 8.0 |
| | Range | (4.4, 10.0) | (5.5, 10.0) |
| | MAP (cmH₂O) | | |
| | N | 9 | 5 |
| | Mean (SD) | 26.1 (4.1) | 25.2 (4.2) |
| | Median | 26.0 | 24.0 |
| | Range | (21.0, 35.1) | (20.9, 32.0) |
| | Inspiratory Time (s) | | |
| | N | 9 | 5 |
| | Mean (SD) | 3.9 (10.9) | 6.8 (14.6) |
| | Median | 0.3 | 0.3 |
| | Range | (0.0, 33.0) | (0.0, 33.0) |
| HFOV 24 Hours (continued) | FiO₂ (%) | | |
| | N | 9 | 5 |
| | Mean (SD) | 54.6 (23.0) | 44.0 (20.4) |
| | Median | 50.0 | 35.0 |
| | Range | (30.0, 100.0) | (32.0, 80.0) |
| | delta P (cmH₂O) | | |
| | N | 9 | 4 |
| | Mean (SD) | 48.2 (15.4) | 41.3 (12.2) |
| | Median | 43.0 | 38.5 |
| | Range | (29.0, 84.0) | (30.0, 58.0) |
| ABG | pH | | |
| | N | 27 | 24 |
| | Mean (SD) | 7.4 (0.1) | 7.4 (0.1) |
| | Median | 7.4 | 7.4 |
| | Range | (7.3, 7.5) | (7.3, 7.5) |
| | PaO₂ (mmHg) | | |
| | N | 27 | 24 |
| | Mean (SD) | 76.1 (23.5) | 71.4 (16.8) |
| | Median | 72.0 | 69.0 |
| | Range | (40.8, 155.9) | (44.7, 102.0) |
| | SaO₂ (%) | | |
| | N | 27 | 24 |
| | Mean (SD) | 94.0 (4.5) | 92.2 (5.4) |
| | Median | 95.9 | 93.0 |
| | Range | (81.0, 100.0) | (72.9, 98.0) |
| ABG 24 Hours (continued) | PaCO₂ (mmHg) | | |
| | N | 27 | 24 |
| | Mean (SD) | 52.1 (11.2) | 47.2 (11.5) |
| | Median | 50.6 | 45.4 |
| | Range | (34.9, 81.5) | (32.4, 85.0) |
| | BE (mEq/L) | | |
| | N | 27 | 24 |
| | Mean (SD) | 4.0 (4.7) | 2.3 (3.8) |
| | Median | 2.6 | 2.8 |
| | Range | (−2.2, 16.0) | (−5.0, 8.0) |
| | HCO₃ (mEq/L) | | |
| | N | 27 | 24 |
| | Mean (SD) | 29.8 (5.6) | 30.6 (14.1) |
| | Median | 29.0 | 28.0 |
| | Range | (21.9, 45.0) | (20.6, 94.0) |
| Extubation Criteria | | | |
| CMV | Rate (/min) | | |
| | N | 23 | 20 |
| | Mean (SD) | 14.3 (8.3) | 16.3 (7.9) |
| | Median | 12.0 | 15.5 |
| | Range | (0.0, 36.0) | (0.0, 34.0) |
| | Pplat (cmH₂O) | | |
| | N | 3 | 3 |
| | Mean (SD) | 18.0 (7.2) | 21.0 (6.2) |
| | Median | 20.0 | 19.0 |
| | Range | (10.0, 24.0) | (16.0, 28.0) |
| CMV Extubation (continued) | PEEP (cmH₂O) | | |
| | N | 25 | 21 |
| | Mean (SD) | 5.8 (0.9) | 5.8 (0.7) |
| | Median | 6.0 | 6.0 |
| | Range | (4.0, 8.0) | (5.0, 8.0) |
| | FiO₂ (%) | | |
| | N | 25 | 21 |
| | Mean (SD) | 39.8 (9.1) | 38.1 (12.5) |
| | Median | 40.0 | 40.0 |
| | Range | (25.0, 60.0) | (0.4, 60.0) |
| | MAP (cmH₂O) | | |
| | N | 24 | 20 |
| | Mean (SD) | 10.5 (3.2) | 10.2 (2.3) |
| | Median | 10.0 | 10.0 |
| | Range | (5.0, 17.0) | (8.0, 18.0) |
| | Set Vt (mL) | | |
| | N | 17 | 10 |
| | Mean (SD) | 169.0 (145.3) | 106.9 (33.6) |
| | Median | 110.0 | 109.5 |
| | Range | (0.0, 450.0) | (55.0, 160.0) |
| | Inspiratory Time (s) | | |
| | N | 20 | 18 |
| | Mean (SD) | 0.9 (0.2) | 0.8 (0.1) |
| | Median | 0.8 | 0.8 |
| | Range | (0.6, 1.6) | (0.5, 1.0) |
| ABG | pH | | |
| | N | 23 | 15 |
| | Mean (SD) | 7.4 (0.1) | 7.4 (0.1) |
| | Median | 7.4 | 7.4 |
| | Range | (7.2, 7.5) | (7.3, 7.5) |
| | PaO₂ (mmHg) | | |
| | N | 23 | 15 |
| | Mean (SD) | 88.4 (26.2) | 91.8 (42.3) |
| | Median | 83.0 | 78.0 |
| | Range | (46.0, 156.0) | (42.0, 212.0) |
| | SaO₂ (%) | | |
| | N | 23 | 15 |
| | Mean (SD) | 95.6 (3.9) | 94.6 (5.9) |
| | Median | 97.0 | 96.0 |
| | Range | (82.0, 100.0) | (76.0, 100.0) |
| | PaCO₂ (mmHg) | | |
| | N | 23 | 15 |
| | Mean (SD) | 45.6 (6.7) | 47.5 (8.4) |
| | Median | 48.0 | 44.0 |
| | Range | (30.8, 53.5) | (33.5, 64.0) |
| | BE (mEq/L) | | |
| | N | 23 | 15 |
| | Mean (SD) | 4.4 (6.7) | 5.0 (2.6) |
| | Median | 2.3 | 4.0 |
| | Range | (−6.0, 23.0) | (1.0, 11.0) |

TABLE 28-continued

Descriptive Statistics for Respiratory
Values by Actual Treatment Received

|  |  | Placebo | Nitric oxide 5 ppm |
|---|---|---|---|
| ABG Extubation (continued) | HCO$_3$ (mEq/L) | | |
|  | N | 23 | 15 |
|  | Mean (SD) | 28.5 (5.4) | 30.2 (2.8) |
|  | Median | 27.5 | 31.0 |
|  | Range | (20.9, 40.0) | (25.4, 37.0) |

Abbreviations:
CMV = conventional mechanical ventilation;
Pplat = plateau pressure;
PEEP = positive end-expiratory pressure;
FiO$_2$ = fraction of inspired oxygen concentration;
MAP = mean airway pressure;
Vt = tidal volume;
HFOV = high-frequency oscillatory ventilation;
delta P = amplitude;
ABG = arterial blood gases;
PaO$_2$ = partial pressure of oxygen;
SaO$_2$ = oxygen saturation (arterial);
PaCO$_2$ = partial pressure of carbon dioxide (arterial);
BE = base excess;
HCO$_3$ = bicarbonate ion.

Discussion and Overall Conclusions

Subjects who received inhaled nitric oxide were no more likely to experience AEs than were those who received placebo, with 21 subjects in the placebo group (72.4%) reporting 93 AEs and 16 subjects in the nitric oxide group (61.5%) reporting 52 AEs. Four AEs, reported by 2 subjects in the placebo group, were suspected to have a relationship to treatment.

The frequencies of treatment discontinuation due to AEs were 6.9% for the placebo group and 3.9% for the nitric oxide group. Compared with subjects treated with placebo, subjects treated with nitric oxide reported fewer serious AEs during the study (27.6% vs. 3.9%) and had a higher survival rate (72.4% vs. 88.5%). No death, serious AE, severe AE, or AE resulting in treatment discontinuation was suspected to be related to study treatment.

Percent methemoglobin levels for subjects who inhaled nitric oxide 5 ppm were equal to or less than those for subjects in the placebo group at most time points during the study, indicating that inhaled nitric oxide is well tolerated and is unlikely to be associated with high levels of methemoglobin at the low dose used in this study.

The safety profile of inhaled nitric oxide 5 ppm appears to compare favorably with that of placebo, with regard to methemoglobin levels, frequency of AEs and, particularly, mortality rates. No serious concerns about the use of inhaled nitric oxide were generated by the results of this study, and it appears that inhaled nitric oxide 5 ppm is safe and well tolerated by children with acute hypoxemic respiratory failure.

What is claimed is:

1. A method of treating acute respiratory distress syndrome (ARDS) in children comprising administering a gas comprising nitric oxide (NO) to a child in need thereof at a dose in the range from about 2 ppm to about 8 ppm NO for a treatment period of at least 24 hours, wherein administration of NO increases the number of days that the child is alive and ventilator-free at 28 days after the start of NO administration.

2. The method of claim 1, wherein NO is administered for a treatment period of at least 2 days.

3. The method of claim 1, wherein NO is administered for a treatment period of at least 3 days.

4. The method of claim 1, wherein NO is administered for a treatment period up to 2 months.

5. The method of claim 1, wherein NO is administered at a dose in the range from about 2 ppm to about 6 ppm NO.

6. The method of claim 1, wherein NO is administered at a dose of about 5 ppm.

7. The method of claim 1, wherein the child is not subjected to extracorporeal membrane oxygenation during NO administration.

8. The method of claim 1, wherein the child is less than 17 years old.

9. The method of claim 1, wherein the child is determined to have a ratio of partial pressure of oxygen in arterial blood to fraction of inspired oxygen (PaO$_2$/FiO$_2$ ratio) of less than 300.

10. A method of treating acute respiratory distress syndrome (ARDS) in children comprising administering a gas comprising nitric oxide (NO) to a child in need thereof at a dose in the range from about 2 ppm to about 6 ppm NO for a treatment period of at least 2 days, wherein administration of NO increases the number of days that the child is alive and ventilator-free at 28 days after the start of NO administration.

11. The method of claim 10, wherein NO is administered for a treatment period of at least 3 days.

12. The method of claim 10, wherein NO is administered for a treatment period up to 2 months.

13. The method of claim 10, wherein NO is administered at a dose of about 5 ppm.

14. The method of claim 10, wherein the child is not subjected to extracorporeal membrane oxygenation during NO administration.

15. The method of claim 10, wherein the child is less than 17 years old.

16. The method of claim 10, wherein the child is determined to have a ratio of partial pressure of oxygen in arterial blood to fraction of inspired oxygen (PaO$_2$/FiO$_2$ ratio) of less than 300.

17. A method of treating acute respiratory distress syndrome (ARDS) in children less than 17 years old, the method comprising administering a gas comprising nitric oxide (NO) to a child in need thereof at a dose of about 5 ppm NO for a treatment period of at least 24 hours, wherein administration of NO increases the number of days that the child is alive and ventilator-free at 28 days after the start of NO administration.

18. The method of claim 17, wherein the child is not subjected to extracorporeal membrane oxygenation during NO administration.

19. The method of claim 1, wherein the child is determined to have an oxygenation index of greater than or equal to 12 cm H$_2$O/mmHg.

20. The method of claim 10, wherein the child is determined to have an oxygenation index of greater than or equal to 12 cm H$_2$O/mmHg.

21. The method of claim 17, wherein the child is determined to have an oxygenation index of greater than or equal to 12 cm H$_2$O/mmHg.

22. The method of claim 1, wherein the child has a chest x-ray showing at least unilateral infiltrates, wherein the x-ray has been taken within 24 hours of starting treatment.

23. The method of claim 10, wherein the child has a chest x-ray showing at least unilateral infiltrates, wherein the x-ray has been taken within 24 hours of starting treatment.

24. The method of claim 17, wherein the child has a chest x-ray showing at least unilateral infiltrates, wherein the x-ray has been taken within 24 hours of starting treatment.

* * * * *